(12) United States Patent
Carell et al.

(10) Patent No.: US 8,193,335 B2
(45) Date of Patent: Jun. 5, 2012

(54) CLICK CHEMISTRY FOR THE PRODUCTION OF REPORTER MOLECULES

(75) Inventors: Thomas Carell, Krailling (DE); Anja Schwögler, Mannheim (DE)

(73) Assignee: baseclick GmbH, Tutzing (DE)

( * ) Notice: Subject to any disclaimer, the term of this patent is extended or adjusted under 35 U.S.C. 154(b) by 194 days.

(21) Appl. No.: 12/447,526

(22) PCT Filed: Oct. 31, 2007

(86) PCT No.: PCT/EP2007/009474
§ 371 (c)(1),
(2), (4) Date: Apr. 28, 2009

(87) PCT Pub. No.: WO2008/052775
PCT Pub. Date: May 8, 2008

(65) Prior Publication Data
US 2010/0081137 A1    Apr. 1, 2010

Related U.S. Application Data

(60) Provisional application No. 60/855,574, filed on Oct. 31, 2006.

(51) Int. Cl.
*C07H 21/00*    (2006.01)
*C07H 21/02*    (2006.01)
*C07H 19/04*    (2006.01)
(52) U.S. Cl. ..................................................... 536/25.3
(58) Field of Classification Search ................. 536/25.3, 536/26.6, 23.1
See application file for complete search history.

(56) References Cited

U.S. PATENT DOCUMENTS

| | | |
|---|---|---|
| 5,705,622 A | 1/1998 | McCapra |
| 6,737,236 B1 | 5/2004 | Pieken et al. |
| 6,884,882 B1 | 4/2005 | Kim et al. |
| 7,427,678 B2 | 9/2008 | Pieken et al. |
| 2003/0171570 A1 | 9/2003 | Schweitzer |
| 2003/0175728 A1 | 9/2003 | Belousov et al. |
| 2005/0032081 A1 | 2/2005 | Ju et al. |
| 2005/0260645 A1 | 11/2005 | Green et al. |
| 2010/0081137 A1 | 4/2010 | Carell et al. |

FOREIGN PATENT DOCUMENTS

| | | |
|---|---|---|
| WO | WO 89/02475 | 3/1989 |
| WO | WO 96/09316 | 3/1996 |
| WO | WO 96/34984 | 11/1996 |
| WO | WO 01/42505 | 6/2001 |
| WO | WO 03/079014 | 9/2003 |
| WO | WO 03/101972 | 12/2003 |
| WO | WO 2006/116629 | 11/2006 |
| WO | WO 2006/117161 | 11/2006 |
| WO | WO 2007/120192 | 10/2007 |

OTHER PUBLICATIONS

International Search Report for International Application No. PCT/EP2007/009474; International Filing Date: Oct. 31, 2007.

International Preliminary Report on Patentability for International Application No. PCT/EP2007/009474; International Filing Date: Oct. 31, 2007.

(Continued)

*Primary Examiner* — Jezia Riley
(74) *Attorney, Agent, or Firm* — Brinks Hofer Gilson & Lione

(57) ABSTRACT

The present invention relates to methods for producing reporter molecules suitable for the detection of analytes, e.g. nucleic acids. Further, the present invention relates to methods and regions for detecting analytes.

18 Claims, 13 Drawing Sheets

OTHER PUBLICATIONS

Figure 1:
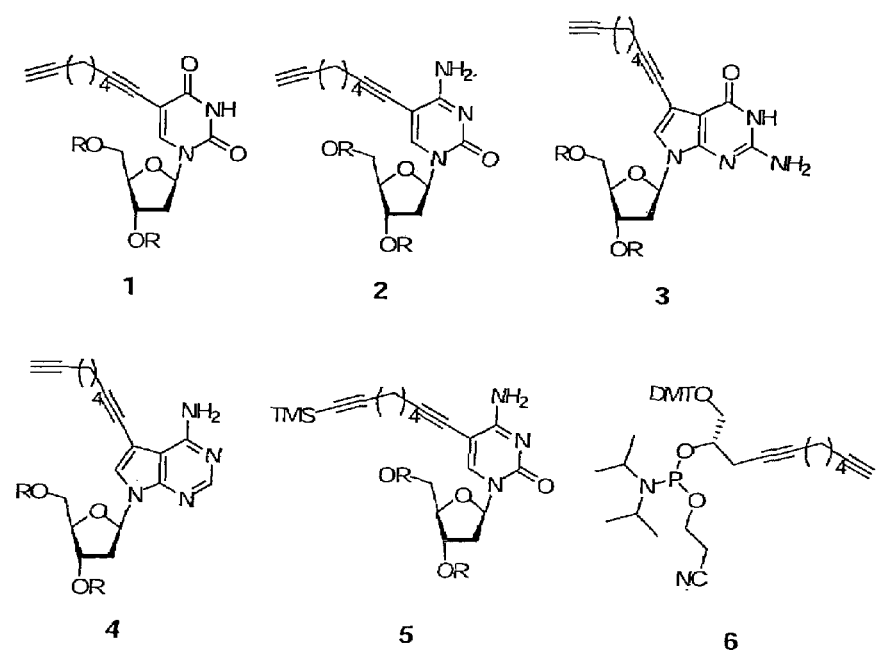

Aucagne Vincent et al.: "Chemoselective formation of successive triazole linkages linkages in one pot: "click-click" chemistry." Organic Letters, vol. 8, No. 20, Sep. 28, 2006, pp. 4505-4507; XPOO0910784, Search Report.

Jang Hangjun et al.: "Click to fit: versatile polyvalent display on a peptidomimetic scaffold." Organic Letters, vol. 7, No. 10, May 12, 2005, pp. 1951-1954, XP000910778, Search Report.

Montagnat et al.: "Synthesis of azide-alkyne fragments' for 'click' chemical applications; formation of oligomers from orthogonally protected trialkylsilyl-propargyl azides and propargyl alcohols" Tetrahedron Letters, Elsevier, Amsterdam, vol. 47, No. 39, Sep. 25, 2006, pp. 6971-6974, XP005614805, Search Report.

Lu Genliang et al.: "An iterative route to "decorated" ethylene glycol-based linkers." Chemical Communications (Cambridge, England), No. 15, Apr. 21, 2006, pp. 1652-1654, XP009107801, Search Report.

Speers A et al.: "Profiling enzyme activities in vivo using click chemistry methods." Chemistry and Biology, Current Biology, London, GB, vol. 11, No. 4, Apr. 1, 2004, pp. 535-546, XP00237Z550, Search Report.

Sieber Stephan A et al.: "Proteomic profiling of metalloprotease activities with cocktails of active-site probes." Nature Chemical Biology, vol. 2, No. 5, May 2006, pp. 274-281, XPOQ9107764, Search Report.

Speers Anna E et al: "A tandem orthogonal proteolysis strategy for high-content chemical proteomics." Journal or the American Chemical Society, vol. 127, No. 28, Jul. 20, 2005, pp. 10018-10019, XP009107850, Search Report.

Ustinov AV et al: "Oligonucleotides containing aryl acetylene residues: Synthesis and post-synthetic modification via [3+2] cycloaddition" Russian Chemical Bulletin, Kluwer Academic Publishers-Plenum Publishers, NE, vol. 55, No. 7, Jul. 1, 2006, pp.' 1268-1274. XP019454004, Search Report.

Gierlich Johannes et al.: ""Click" chemistry as a reliable method for the 'high-density postsynthetic functionalization of alkyne-modified DNA. Organic Letters, vol. 8, No. 17, Aug. 17, 2006, pp. 3639-3642, XP009107846, Search Report.

Baruch Amos et al.: "Enzyme activity: It's all about image." Trends in Cell Biology, Elsevier Science Ltd, XX, vol. 14, No. 1, Jan. 1, 2004, pp. 29-35, XP002309365, Search Report.

Fischer Rainer et al.: "A targeted protease substrate for a quantitative determination of protease activities in the endolysosomal pathway." Chembiochem—A European Journal of Chemical. Biology, Wiley VCH, Weinheim, DE, vol. 7, No. 9, Sep. 1, 2006, pp. 1428-1434, XP002442P94, Search Report.

Kolb H.C. et al.: •"The• growing impact of click chemistry on drug discovery." Drug Discovery Today, Elsevier, Rahway, NJ, US, vol. 8, .No. 24, Dec. 15, 2003, pp. 1128-1137, XP002377521, Search Report.

Geci I. et al.: "Synthesis of twisted intercalating nucleic acids possessing acridine derivatives. Thermal stability studies." Bioconjugate Chemistry, ACS, Washington, DC, US, vol. 17, No. 4, Jun. 21, 2006, pp. 950-957, XP002399203, Search Report.

Extended European Search Report for EP Application No. 10171611 dated Oct. 13, 2010.

Extended European Search Report for EP Application No. 10171618. 1, Completion Date: Sep. 30, 2010; Mailing Date: Nov. 9, 2010.

International Preliminary Report on Patentability for International Application No. PCT/EP2006/004017 and European Search Report, 2007.

Russian Office Action dated Sep. 15, 2009, RU Application No. 2007 144 529.

Berthod, T. et al., "Synthesis and mass spectrometry analysis of oligonucleotides bearing 5- formyl 1-2'-deoxyuridine in their structures", Nucleosides and Nucleotides, vol. 15, No. 7-8, 1996, pp. 1287-1305, XP 002383615.

Buff, R. et al., "Z-DNA formation by 2'-C-ethynyl-modified oligonucleotides", Synlett 1999 Germany, No. SPEC, ISS, 1999, pp. 905-908, XP002383614.

Burley, G. et al., "Directed DNA Metallization" J. Am. Chem. Soc. 2006, 128, 1398-1399 and S1-S21.

Burley, G. et al., "New labeling strategies for the sensitive detection of nucleic acids". Chemistry of Nucleic Acid Components, Acad. Sci. Czech Republic, Inst. Organic Chem. & Biochemistry, Felingovoniam 2, Prague 166106, Czech Republic Series: Collection Symposium Series, 2005, pp. 229-232 XP008068569 & 13$^{th}$ Symposium on Chemistry Nucleic Acid Components; Spindelruv Mlyn, Czech Republic, Sep. 2005.

Deiters, A. and Schultz P.G., "In vivo incorporation of an alkyne into proteins in *Escherichia coli*", Bioorganic & Medicinal Chemistry Letters, vol. 15, No. 5, Mar. 1, 2005, pp. 1521-1524, XP 004750702.

Dobrikov et al., "Sensitized photomodification of DNA by binary system of oligonucleotide conjugates. III. Two-photon sensitization", Bioorganics, 1998, 24:11, 831-838.

Fischler, M et al., "Chain-like assembly of gold nanoparticles on artificial DNA templates via 'click chemistry'", Chem. Commun., 2008, 169-171.

Fischler, M. et al., "Formation of Bimetallic Ag-Au Nanowires by Metallization of Artificial DNA Duplexes" Small, 2007, 3, No. 6, 1049-1055.

Gierlich, J. et al., "Synthesis of Highly Modified DNA by a Combination of PCR with Alkaline-Bearing Triphosphates and Click Chemistry" Chem. Eur. J., 2007, 13, 9486-9494 and S1-S27.

Gramlich, P.M.E. et al., "Synthesis of Modified DNA by PCR with Alkyne-Bearing Purines Followed by a Click Reaction", Org. Lett., 2008, 10, No. 2, 249-251 and S1-S16.

Higashiya, S. et al., "A facile synthesis of 2-azidoadenosine derivatives from guanosine as photoaffinity probes", Bioorganic & Medicinal Chemistry Letters, Oxford, GB, vol. 6, No. 1, Jan. 9, 1996, pp. 39-42, XP004135119.

Held, A. H. et al., "Challenging artificial genetic systems: thymidine analogs with 5-position sulfur functionality" Nucleic Acids Research, 2002, vol. 30, No. 17, 3857-3869.

Hyde, Robyn M. et al., "Antiviral amphipathic oligo- and polyribonucleotides: Analogue development and biological studies", Journal of Medicinal Chemistry, vol. 46, No. 18, May 8, 2003, pp. 1878-1885, XP002383613.

Kagel, John R. et al., "A chemical model for the fragmentation reaction in thymidylate synthase catalysis: Synthesis and evaluation of 5-methylene-1-(1,2,3,4-tetrahydroquinolyl)-6-allyluridine", Journal of Organic Chemistry, vol. 58, No. 10, 1993, pp. 2738-2746 XP002383617.

Kaoru Okamoto et al., "Synthesis of ara-cadeguomycin. 2-amino-3,4-dihydro-4-oxo-7-(beta-d-arabinofuranosyl)-7h__pyrrolo[2,3-d]pyrimidine-5-carboxylic acid", Bulletin of The Chemical Society of Japan, Chemical Society of Japan, Tokyo, JP, vol. 59, No. 6, Jun. 1, 1986, pp. 1915-1919 XP 000601944.

Kolb, H.C. et al., "Click Chemistry: Diverse chemical function from a few good reactions", Angewandte Chemie, International Edition, vol. 40, 2001, pp. 2004-2021, XP 001206265.

Kolb, H.C. and Sharpless, K.B., "The growing impact of click chemistry on drug discovery", Drug Discovery Today, vol. 8, No. 24, Dec. 15, 2003, pp. 1128-1137, XP 002377521.

Lee Lac V. et al., "A potent and highly selective inhibitor of human alpha-1,3-fucosyltransferase via click chemistry", Journal of the American Chemical Society, vol. 125, No. 32, Aug. 13, 2003, pp. 9588-9589, XP002383611.

Malakhov et al., "Synthesis of a new fluorescent 9,10-bisphenylethynylanthracene-derived pseudonucleoside and its introduction into oligonucleotides", Bioorganics, 1999, 25:12, 933-937.

Marsh, Andrew J. et al., "The synthesis and properties of oligoribonucleotide-spermine conjugates" Organic & Biomolecular Chemistry, Jul. 21, 2004, vol. 2, No. 14, pp. 2103-2112 XP 002383616.

Martin, R. et al., "A highly sensitive, nonradioactive DNA labeling and detection system", Biotechniques, Natick, MA, US; 9(6), (1990), 762-766. XP000606333.

Matsuo, T., "In situ visualization of messenger RNA for basic fibroblast growth factor in living cells", Biochimica et Biophysica Acta, 1379 (2), (1998), 178-184. XP002602819.

Minakawa, N. et al., "A versatile modification of on-column oligodeoxynucleotides using a copper-catalyzed oxidative acetylenic coupling reaction" Journal of the American Chemical Society, Sep. 24, 2003, vol. 125, No. 38, pp. 11545-11552, XP002383619.

Nam, N. H. et al., "ATP-phosphopeptide conjugates as inhibitors of src tyrosine kinases", Bioorganic and Medicinal Chemistry, Elsevier Science Ltd., GB, vol. 12, No. 22, Nov. 15, 2004, pp. 5753-5766, XP 004604949.

Nguyen, H.K. et al., "Studies towards the design of a modified GC base pair with stability similar to that of the AT base pair", Tetrahedron Letters, vol. 38, No. 23, 1997, pp. 40983-4086, XP 002041345.

Riggins, James et al., "Kinetic and thermodynamic analysis of the hydrolytic ring-opening of the malondialydehyde-deoxyguanosine adduct, 3-(2'-deoxy-beta-D-erythro pentofuranosyl)-pyrimido[1,2-alpha]purin-10(3H)-one", Journal of the American Chemical Society, Jul. 7, 2004, vol. 126, No. 26, pp. 8237-8243, XP002383618.

Santangelo, P. et al., "Dual FRET molecular beacons for mRNA detection in living cells", Nucleic Acids Research, 32(6), (2004), 1-9. XP002602820.

Seo Tae Seok et al., "Click chemistry to construct fluorescent oligonucleotides for DNA sequencing", Journal of Organic Chemistry, vol. 68, No. 2, Dec. 21, 2002, pp. 609-612, XP 0022387640.

Sivakumar, K. et al., "A fluorogenic 1,3-dipolar cycloaddition reaction of 3-azidocoumarins and acetylenes", Organic Letters, vol. 6, No. 24, 2004, pp. 4603-4606, XP 002995168.

Trevisoiol, E. et al., "The oxyamino-aldehyde coupling reaction: An efficient method for the derivatization of oligonucleotides", Tetrahedron Letters, vol. 38, No. 50, 1997, pp. 8787-8690.

Venyaminova S.G. et al., "New photoreactive mRNA analogues for the affinity labeling of ribosomes", Nucleosides and Nucleotides, vol. 14, No. 3-5, 1995, pp. 1069-1072.

Wirges, C.T. et al., "Pronounced Effect of DNA Hybridization on Click Reaction Efficiency" QSAR Comb. Sci. 26, 2007, No. 11-12, 1159-1164.

Youngjoo, Byum et al., "Synthesis and biological evaluation of neutral and zwitterionic 3-carboranyl thymidine analogues for boron neutron capture therapy". Journal of Medicinal Chemistry, vol. 48, No. 4, Feb. 24, 2005, pp. 1188-1198, XP002383612.

Wang Q. et al.: "Bioconjugation by Copper(I)-Catalyzed Azide-Alkyne [3+2] Cycloaddition." Journal of the American Chemical Society, vol. 125, No. 11, Mar. 9, 2003, pp. 3192-3193, XP008128703, EP Search Report.

Lin H. et al.: "A Chemoenzymatic Approach to Glycopeptide Antibiotics." Journal of the American Chemical Society, vol. 126, No. 43, 2004, pp. 13998-14003, XP002632941, EP Search Report.

Extended European Search Report for EP Application No. 10177873. 6, Completion Date: Apr. 14, 2011, Mailing Date: May 16, 2011.

De Clercq, E. et al., "(E)-5-(2-Bromovinyl)-2'-deoxyuridine: A potent and selective anti-herpes agent", Proc. Natl. Acad. Sci., vol. 76, No. 6, Jun. 1979, pp. 2947-2951.

Otvos, L., et al., "Base Modified Oligodeoxynucleotides. II. Increase of Stability to Nucleases by 5-Alkyl-, 5-(1-Alkenyl)-, and 5-(1-Alkynyl)-pyrimidines", Nucleosides, Nucleotides and Nucleic Acids, vol. 18, No. 9, 1999, pp. 1929-1933.

37

38

```
                        SEQUENCE LISTING

<160> NUMBER OF SEQ ID NOS: 4

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 5-(8-trimethylsilylocta-1,7-diinyl)-5'-O-(4,4'-
      dimethoxytrityl)-3'-O-((2-cyanoethoxy)(diisopropylamino)
      phosphino)-2'-(N-benzoyl)desoxycytidine
<220> FEATURE:
<221> NAME/KEY: modified_base
<222> LOCATION: (13)..(13)
<223> OTHER INFORMATION: 5-(octa-1,7-diinyl) modified 2'-desoxyuridine

<400> SEQUENCE: 1
gcgcngttca ttngcg                                                     16

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 5-(8-trimethylsilylocta-1,7-diinyl)-5'-O-(4,4'-
      dimethoxytrityl)-3'-O-((2-cyanoethoxy)(diisopropylamino)
      phosphino)-2'-(N-benzoyl)desoxycytidine
<220> FEATURE:
<221> NAME/KEY: modified_base
<222> LOCATION: (12)..(12)
<223> OTHER INFORMATION: 5-(octa-1,7-diinyl) modified 2'-desoxyuridine

<400> SEQUENCE: 2
cgcnacacga anccg                                                      15

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 5-(8-triisopropylsilylocta-1,7-diinyl)-5'-O-
      (4,4'-dimethoxytrityl)-3'-O-((2-cyanoethoxy)(diisopropylamino)
      phosphino)-2'-(N-benzoyl)desoxycytidine
<220> FEATURE:
<221> NAME/KEY: modified_base
```

```
<222> LOCATION: (13)..(13)
<223> OTHER INFORMATION: 5-(octa-1,7-diinyl) modified 2'-desoxyuridine

<400> SEQUENCE: 3
gcgcngttca ttngcg                                                        16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 5-(8-trimethylsilylocta-1,7-diinyl)-5'-O-(4,4'-
      dimethoxytrityl)-3'-O-((2-cyanoethoxy)(diisopropylamino)
      phosphino)-2'-(N-benzoyl)desoxycytidine
<220> FEATURE:
<221> NAME/KEY: modified_base
<222> LOCATION: (9)..(9)
<223> OTHER INFORMATION: 5-(octa-1,7-diinyl) modified 2'-desoxyuridine
<220> FEATURE:
<221> NAME/KEY: modified_base
<222> LOCATION: (13)..(13)
<223> OTHER INFORMATION: 5-(8-triisopropylsilylocta-1,7-diinyl)-5'-O-
      (4,4'-dimethoxytrityl)-3'-O-((2-cyanoethoxy)(diisopropylamino)
      phosphino)-2'-(N-benzoyl)desoxycytidine

<400> SEQUENCE: 4
gcgcngttna ttncgc                                                        16
```

CLICK CHEMISTRY FOR THE PRODUCTION OF REPORTER MOLECULES

This application is a National Stage application of International Application No. PCT/EP2007/009474 filed Oct. 31, 2007, which claims the benefit of U.S. Provisional Application No. 60/855,574, filed Oct. 31, 2006, the entire contents of which is hereby incorporated herein by reference.

SEQUENCE LISTING

The instant application contains a Sequence Listing which has been submitted via EFS-Web and is hereby incorporated by reference in its entirety. Said ASCII copy, created on Nov. 16, 2009, is named 139784.txt, and is 2,733 bytes in size.

The present invention relates to methods for producing reporter molecules suitable for the detection of analytes, e.g. nucleic acids. Further, the present invention relates to methods and regions for detecting analytes.

BACKGROUND OF THE INVENTION

Landmark breakthroughs in the field of DNA synthesis, most importantly the Polymerase Chain Reaction (PCR) and the phosphoramidite chemistry, have lead to an increasing repertoire of modifications of natural DNA. In PCR, modified nucleoside triphosphates carrying a linker on the 5-position of pyrimidines or on the 7-position of 7-deazapurines can be incorporated using certain Family B polymerases [1]. The ease of incorporation of these building blocks into DNA strongly depends on the steric bulk and the molecular structure of the side chain. In principle all four naturally occurring nucleobases can be replaced by modified ones in a PCR [2]. If phosphoramidite chemistry is employed, in principle any molecular structure can be incorporated into DNA. The biggest limitation is that the modified nucleobases that are incorporated into DNA must be stable towards the conditions of phosphoramidite DNA synthesis and deprotection of the resulting DNA strand.

An approach circumventing both the problems of steric bulk as well as the potential chemical lability of the modifications has been developed in our group [3]. The modified nucleotides carry a linker containing an internal and a terminal alkyne. The internal alkyne facilitates incorporation via PCR as the steric bulk in close proximity to the nucleobase is minimized. The terminal alkyne is a reactive site for the Click reaction [4], which is a copper-catalysed Huisgen dipolar cycloaddition between azides and alkynes [5]. This reaction can be conveniently used for the postsynthetic labelling of biomolecules. Azides can thus be attached to DNA in a high-yielding reaction without encountering any significant side reactions, as natural biomolecules do not carry any azides or terminal alkynes. This approach is also described in PCT/EP2006/004017 the content of which is herein incorporated by reference.

According to previously described procedures only a single type of labelling group can be introduced in a site-selective manner. Thus it was an object of the present invention to overcome this limitation and allow the site-specific labelling of reporter molecules with at least two different labelling groups, e.g. dyes or other functional molecules in a consecutive way, thereby realizing an unprecedented versatility in modification.

SUMMARY OF THE INVENTION

The present invention allows the site-specific incorporation of two or more different functional groups into a reporter molecule in a consecutive manner. This is achieved by incorporating at least two different handle groups into the reporter molecule during its synthesis which may be selectively coupled to reaction partners comprising different functional groups.

Thus, a first aspect of the present invention relates to a method for producing a reporter molecule comprising at least two different functional groups, wherein at least one first and at least one second handle group are incorporated into the reporter molecule wherein the handle groups are selected from an alkyne group, a protected alkyne group, an azide group, an aldehyde group, a protected aldehyde group, a hydrazine group or a hydroxylamino group, and wherein the first and second handle groups are different and wherein the first and second handle groups are selectively coupled to first and second reaction partners comprising different first and second functional groups.

A further aspect of the present invention relates to a method producing a reporter molecule comprising at least two different functional groups, comprising (a) synthesizing the reporter molecule from a plurality of building blocks, wherein at least one building block comprises a first handle group which is selected from an alkyne group, a protected alkyne group, an azide group, aldehyde group, a protected aldehyde group, a hydrazine group or a hydroxylamino group, wherein at least one building block comprises a second handle group which is selected from an alkyne group, a protected alkyne group, an azide group, aldehyde group, a protected aldehyde group, a hydrazine group or a hydroxylamino group, and wherein the first handle group is different from the second handle group;

(b) coupling a first reaction partner to the first handle group under conditions wherein the first handle group is reactive and the second handle group is not reactive, wherein the first reaction partner comprises a first functional group and subsequently (c) coupling a second reaction partner to the second handle group wherein the second reaction partner comprises a second functional group and wherein the first functional group is different from the second functional group.

A further aspect of the invention refers to a method for detecting an analyte in a sample comprising the steps:

(a) providing a sample;
(b) contacting the sample with a reporter molecule comprising at least two different functional groups wherein the functional groups are bound to the reporter molecule via linker groups comprising a 1,2,3-triazole rings and
(c) detecting an interaction of the reporter molecule with the analyte which is indicative for the presence and/or amount of analyte in the sample.

A further aspect of the invention is a receptor molecule comprising at least two different functional groups wherein the functional groups are bound to the reporter molecule via linker groups comprising a 1,2,3-triazole rings.

A further aspect of the invention is a compound of the Formula (I)

wherein
C is a protected alkyne group,
S is a spacer or a bond, and
N is a nucleic acid or nucleic acid analogue building block such as a nucleosidic or nucleotidic or non-nucleosidic compound.

Yet a further aspect of the invention is a compound of the Formula (II)

wherein
B is biotin or a biotin derivative such as desthiobiotin or aminobiotin,
S is a spacer or a bond and
$N_3$ is an azide group.

Still a further aspect of the invention is a compound of the Formula (III)

Q-S-N wherein
Q is a quencher group,
S is a spacer or a bond and
N is an azide group.

Furthermore, the invention refers to a compound of the Formula (IV)

Z-S-N wherein
Z is an aldose group, wherein the hydroxy groups are protected with acyl and/or silyl groups, or a protected or an unprotected 1,2 diol group
S is a spacer or a bond, and
N is a nucleic acid or nucleic acid analogue building block such as a nucleosidic or nucleotidic compound.

Further, the invention refers to a compound of the Formula (V)

D-S-N wherein
D is an Infrared (IR) dye,
S is a spacer or a bond and
N is an azide group.

The compounds of Formulae (I)-(V) are suitable as reagents in methods for detecting analytes, particularly by photographic methods as described below in detail.

The present invention allows an efficient production of reporter molecules comprising two, three or more different functional groups. These reporter molecules allow a highly sensitive detection of an analyte, e.g. nucleic acids or nucleic acid binding proteins, in biological samples, e.g. clinical samples, environmental samples or agricultural samples. Preferred applications include, but are not limited to, the detection of genetic variabilities, e.g. single nucleotide polymorphisms (SNPs), pesticide or medicament resistances, tolerances or intolerances, genotyping, e.g. the detection of species or strains of organisms, the detection of genetically modified organisms or strains, or the detection of pathogens or pests, and the diagnosis of diseases, e.g. genetic diseases, allergic diseases, autoimmune diseases or infectious diseases. A further preferred application is the detection of nucleic acids in samples for brand protection, wherein products such agricultural products, food products, or goods of value and/or packaging of these products are encoded with product-specific information, e.g. but not limited to production site, date production, distributor etc., and wherein this information is detected with the methods and reagents as described above.

DETAILED DESCRIPTION OF PREFERRED EMBODIMENTS

A first aspect of the invention refers to the production of a reporter molecule. The reporter molecule can be any type of molecule which is suitable for diagnostic applications and which may be functionalized with at least two, e.g. two, three, four or more different functional groups by selective coupling reactions. For example, the reporter molecule may be a nucleic acid molecule, a nucleic acid analogue molecule or a peptide. Preferably, the reporter molecule is synthesized from building blocks, e.g. monomeric building blocks like amino acids, nucleotides or nucleotide analogues. The synthesis may involve a chemical synthesis, e.g. a chemical solid phase synthesis or an enzymatic synthesis, e.g. an enzymatic nucleic acid synthesis by primer elongation. Preferably, the reporter molecule comprises at least 4, more preferably at least 6 and most preferably at least 10 building blocks. Although reporter molecules with a length of several hundred and up to thousands of building blocks may be used, an upper length of up to 300 building blocks is preferred. More preferably, the length is up to 200 and most preferably up to 100 building blocks.

The functional groups are preferably selected from labelling groups, such as dyes, particularly fluorescent dyes, photosensitizer groups, quencher groups and attachment groups. Labelling groups may be direct labelling groups, i.e. groups which generate a detectable signal or indirect labelling groups, i.e. groups which cause generation of a detectable signal by different groups.

In an especially preferred embodiment, the labelling groups are fluorescent dyes, e.g. blue, red, or green fluorescent dyes such as cyanine dyes or merocyanine dyes. Particularly preferred are IR-dyes. These dyes may be functionalized to azide derivatives as described in Example 18.

Quencher groups are groups capable of quenching the fluorescence emissions from fluorescent groups. Quencher groups may be selected from known quencher groups, e.g. quencher groups in Molecular Beacon reporter molecules as described in references [12-16].

Attachment groups are groups for attaching a specific binding partner via high affinity interactions. Specific examples of attachment groups are biotin or biotin derivatives such as desthiobiotin, or aminobiotin, or haptens, e.g. low molecular weight groups (e.g. molecular weight $\leq 2000$) specifically capable of interacting with an antibody such as trinitrophenyl or peptide epitopes such as the FLAG sequence.

The invention comprises the coupling of different functional groups to the reporter molecule. The different functional groups preferably comprise at least one labelling group. In an especially preferred embodiment, the first functional group is a labelling group and the second functional group is a quencher group or an attachment group.

When the first functional group is a labelling group and the second functional group is a quencher group, the reporter molecule may be a Molecular Beacon (MB). Molecular Beacons are single-stranded hybridization probes, e.g. nucleic acid or nucleic acid analogue probes that form a stem-and-loop structure. The loop may contain a probe sequence that is complementary to a target sequence, and the stem is formed by the annealing of complementary arm sequences that are located on either side of the probe sequence. A labelling group, e.g. a fluorophore, is preferably linked to the end of one arm and a quencher is linked to the other arm. Molecular Beacons do not fluoresce when they are free in solution. However, when they hybridise to a nucleic acid strand containing a target sequence, they undergo a conformational change that results in a bright fluorescence. The length of Molecular Beacon reporter molecules is preferably 15-100 and more preferably 20-50 nucleotide or nucleotide analogue building blocks.

In a further embodiment, the first and second functional groups are labelling groups capable of fluorescence resonance energy transfer (FRET).

The method of the invention involves the incorporation of at least two different types of handle groups into the reporter molecule to which at least two different types of functional groups may be coupled. According to the present invention, the handle groups are selected from unprotected or protected alkyne groups, azide groups, aldehyde groups, protected aldehyde groups, hydrazine groups or hydroxylamino groups, wherein the first and the second handle groups are different.

In a preferred embodiment, the handle groups are selected from alkyne groups, wherein the first handle group may be an unprotected alkyne group and the second handle group may be a protected alkyne group or wherein the first handle group may be a first protected alkyne group and the second alkyne group may be a second protected alkyne group, wherein the first and second protection groups are different and wherein the first protection group may be selectively removed from the reporter molecule without removing the second protection group. Suitable protection groups are e.g. silyl groups as described in reference [6], particularly tri(alkyl/aryl)silyl groups such as trimethylsilyl (TMS), triethylsilyl (TES), tri-isopropylsilyl (TIPS), triphenylsilyl or tert-butyl-dimethylsilyl (TBDMS). Silyl protecting groups may be removed from the alkyne groups by treatment with acid and/or fluorides. Small silyl protection groups such as TMS are labile and may be removed under mild conditions, whereas bulkier silyl protection groups such as TBDMS or TIPS require harsher conditions for removal.

The method of the invention comprises a selective coupling of the first reaction partner to the first handle group on the reporter molecule under conditions where the first handle group is unprotected and thus capable of reaction and the second handle group is not reactive, e.g. due to the presence of a protection group. Alkyne groups may be coupled to a reaction partner with an azide group via a Click reaction, i.e. a (3+2) cycloaddition between azide and alkyne groups which results in the formation of 1,2,3-triazole rings. The Click reaction is preferably carried out in the presence of copper ions, e.g. with CuBr, tris(1-benzyl-1H-1,2,3-triazol-4-yl)methyl]amine (TBTA) and ascorbate.

In a further preferred embodiment, the handle group may be selected from aldehyde groups, particularly from protected aldehyde groups containing different types of protection groups. Aldehyde groups may react with hydrazine ($H_2N$—NH) groups or hydroxylamino ($NH_2$—O) groups to hydrazones (—C=N—NH—) or oximes (C=N—O—). The CN double bond may optionally be reduced by treatment with a reducing agent such as $NaBH_4$.

A preferred protected aldehyde group is an acetal or hemiacetal group which can be converted into a free aldehyde group by treatment with acids, e.g. organic or inorganic acids. Preferred examples of acetal or hemiacetal groups are acetal groups formed with a polyalcohol such as propane diol or ethylene glycol, or hemiacetal groups in a sugar or in a sugar-related compound such as an aldose sugar, e.g. glucose or galactose. Further examples of protected aldehyde groups are imino groups (e.g. =NH groups), which give aldehyde groups upon treatment with acids, thioacetal or dithioacetal groups (e.g. $C(SR)_2$ groups wherein R may be an alkyl radical) which give aldehyde groups upon treatment with mercury salts, oxime groups (e.g. =NOH groups), which give aldehyde groups upon treatment with acids, hydrazone groups (e.g. =N—NHR groups wherein R may be an alkyl radical) which give aldehyde groups upon treatment with acids and imidazolone or imidazolidine groups or benzothiazole or dihydrobenzothiazole groups which give aldehydes upon hydrolysis, e.g. with acid.

Especially preferred protected aldehyde groups are aldose groups, e.g. triose, tetrose, pentose or hexose in cylic form, wherein the hydroxy groups are protected with suitable protection groups, particularly acyl or silyl groups. Acyl protection groups, e.g. acetyl, butyryl, pivaloyl or other aliphathic and/or aromatic carboxylic acid protection groups may be removed under alkaline conditions. Silyl groups may be removed by treatment with acid and/or fluoride. In a further preferred embodiment, the protected aldehyde group is a protected or unprotected 1,2-diol group, which may be reacted with an oxidant such as $NaIO_4$ to give free aldehyde groups.

The present invention also allows incorporation of more than two different handle groups into a reporter molecule. In this case, the first handle group may be an unprotected group alkyne group. The second handle group may be a first protected group, e.g. a first protected alkyne group which may be cleaved off under first deprotection conditions. The third handle group may be a second protected group, e.g. second protected alkyne group which is stable under the first deprotection conditions which result in deprotection of the first protected group and which may be cleaved off under second deprotection conditions which are different from the first deprotection conditions. Specific examples of first and second protected groups are TMS and TIPS. TMS may be cleaved off under mild acidic conditions, e.g. 1% acetic acid. TIPS is stable under these conditions and may be cleaved off by fluoride treatment, e.g. with tetra-n-butyl ammonium fluoride (TBAF) in acetonitrile/DMF.

Figure 17:
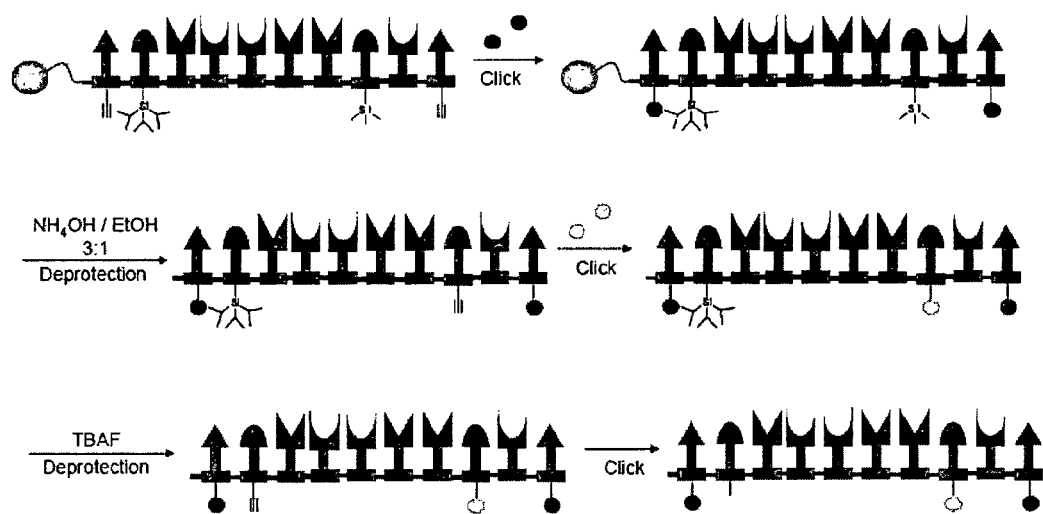
Figure 18:
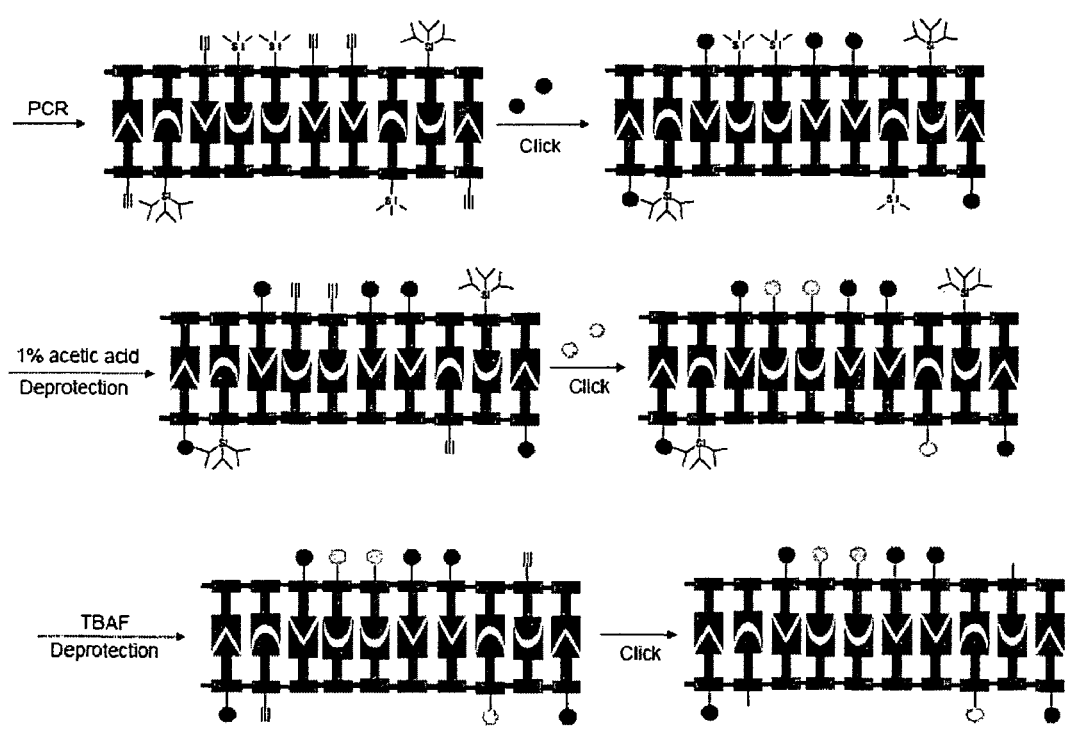

The synthesis of the reporter molecule may comprise a chemical synthesis (e.g. FIG. 17) or enzymatic synthesis (e.g. FIG. 18). Preferably, the synthesis is a chemical synthesis, e.g. a chemical solid phase synthesis wherein the reporter molecule is synthesized by stepwise assembly of building blocks while being bound to a solid phase. The successive coupling of the first reaction partner and the second reaction partner and optionally further reaction partners may take place at different steps during a chemical synthesis procedure. For example, at least the first reaction partner may be coupled while the reporter molecule is bound to the solid phase. In this case, the coupling of the second reaction partner and optionally further reaction partners may take place while the reporter molecule is also still bound to the solid phase or after cleavage of the reporter molecule from the solid phase. On the other hand, it is possible that the first reaction partner is coupled in solution after the reporter molecule has been cleaved off the solid phase. In this case, stepwise deprotection and coupling of further reaction partners also takes place in solution.

A further aspect of the invention refers to the method for detecting an analyte in a sample using a reporter molecule which comprises two different functional groups wherein the functional groups are bound to the reporter molecule via linker groups comprising 1,2,3-triazole rings. These linker groups result in from carrying out a Click reaction involving the coupling of the at least two different functional groups via a Click reaction between an alkyne and an azide group to the backbone of the reporter molecule.

The detection may be a qualitative detection, e.g. the determination of the presence or absence of an analyte, e.g. a specific nucleic acid sequence in the sample to be analysed. The invention, however, also allows quantitative detection of an analyte, e.g. a nucleic acid sequence, in the sample to be analysed. Qualitative and/or quantitative detection may comprise the determination of labelling groups according to methods known in the art.

The analyte to be detected is preferably selected from nucleic acids and nucleoside-, nucleotide- or nucleic acid-binding molecules, e.g. nucleoside-, nucleotide- or nucleic acid-binding proteins. More preferably, the analyte is a nucleic acid, e.g. any type of nucleic acid which can be detected according to known techniques, particularly hybridization techniques. For example, nucleic acid analytes may be selected from DNA, e.g. double-stranded or single-stranded DNA, RNA, or DNA-RNA hybrids. Particular examples of nucleic acid analytes are genomic DNA, mRNA or products derived therefrom, e.g. cDNA. Further, the nucleic acid analytes may be DNA fragments, which are joined by a ligase from a plurality of e.g. 2 sub-fragments.

The method of the invention can be carried out according to any known test format which is suitable for the detection of analytes, particularly nucleic acid analytes in a sample. For example, the method may involve the detection of analytes immobilized on solid surfaces such as membranes, e.g. in Southern or Northern blots, chips, arrays or particles such as beads. Further, the detection can be carried out in gels, e.g. after electrophoretic separation of the sample in gels, e.g. agarose or polyacrylamide gels. The method may involve the detection of single analytes or the parallel detection of a plurality of analytes, e.g. in a chip or microarray format.

In a preferred embodiment the detection involves irradiating a photosensitive medium in the presence of a sample suspected to contain the analyte and a reporter molecule which comprises photosensitizer labelling groups, e.g. fluorescent groups, capable of effecting an energy transfer to the photosensitive medium wherein marker groups may be formed in the medium. Preferably, a reporter molecule is used wherein the photosensitizer group is quenched in the absence of analytes. In the presence of analyte, the quenching of the photosensitizer group is reduced or terminated.

Due to its high sensitivity, the method of the present invention is suitable for detecting analytes directly without amplification. According to the invention, even minute amounts of analytes, e.g. of nucleic acids, e.g. 0.1 ng or lower, preferably 0.01 ng or lower, more preferably 1 pg or lower, still more preferably 0.1 pg or lower, even more preferably 0.01 pg or lower and most preferably 0.001 pg or lower may be determined even without amplification. An especially high sensitivity may be obtained by incorporating multiple labelling groups into a reporter molecule. For example, the detection of an analyte, e.g. a gene, in a biological sample, might be performed by a combination of Southern blotting and the inventive method. It should be noted, however, that the method of the present invention also allows the detection of nucleic acids combined with an amplification step, which may be carried out according to known protocols such as PCR or modifications thereof, such as asymmetric PCR, real-time PCR, reverse transcription PCR, etc, or other amplification protocols such as LCR.

In a preferred embodiment of the invention, a sequence-specific detection of the analyte is carried out, wherein for example a nucleic acid having a specific sequence is distinguished from other nucleic acid sequences in the sample or a polypeptide capable of binding a specific nucleic acid sequence is distinguished from other polypeptides in the sample. Such a sequence-specific detection preferably comprises a sequence-specific hybridization reaction by which the nucleic acid sequence to be detected is associated with a compound carrying a marker group or a marker precursor group. It should be noted, however, that the present invention also allows sequence-unspecific detection of nucleic acids, e.g. detection of any nucleic acids present in a sample.

The handle group is attached to a building block which is suitable for the synthesis of the reporter molecule. Preferably, the handle group is attached to a nucleobase which may be selected from naturally occurring and non-naturally occurring purine and pyrimidine bases. Preferably, the nucleobases are selected from cytidine, uracil, thymine, adenine, guanine, 7-deazaadenine, 7-deazaguanine, inosine and xanthine. The handle group is preferably attached to position 5 or 6, more preferably to position 5, of a pyrimidine nucleobase or to position 7 or 8, more preferably to position 7 of a purine nucleobase, particularly if an enzymatic incorporation into a nucleic acid is desired.

Alternatively, the handle group may also be attached to phosphate or sugar groups of nucleotide building blocks.

Further, the present invention also allows incorporation of non-nucleoside building blocks carrying handle groups into a reporter molecule. Preferred non-nucleoside building blocks having the general Formula (V):

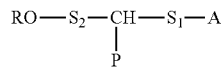

wherein
A is a protected or unprotected alkyne group,
$S_1$ and $S_2$ are in each case independently a non-nucleosidic group, e.g. a spacer or a bond, e.g. $S_1$ is a spacer as defined below and $S_2$ is a covalent bond,
P is a phosphate or phosphate analog group, e.g. a phosphoramidite group, and
R is a coupling group for nucleic acid synthesis, e.g. a dimethoxytrityl (DMT) group.

The handle group may be covalently attached to the building block, e.g. via a direct bond or a spacer, e.g. a spacer having a chain length up to 20 atoms. The spacer may be a flexible spacer, e.g. an alkylene-based spacer, optionally containing heteroatoms such as O, S, and/or N or an at least partially rigid spacer, e.g. a spacer which comprises at least one rigid group selected from alkene groups, alkyne groups, cyclic groups, particularly aromatic or heteroaromatic groups, but also cycloaliphatic groups and combinations thereof. If the building block compound comprises an alkyne or azide, an attachment of the functional group via a direct bond, a flexible spacer or an partially rigid spacer is preferred wherein the flexible spacer could for example have a chain length up to 6 atoms, more particularly up to 4 atoms, and wherein a partially rigid spacer preferably has a chain length of up to 20 atoms, e.g. up to 10 atoms and comprises at least one rigid group as defined above, particularly an alkyne group, and at least one flexible group, e.g. an alkylene group. If on the other hand, the handle group is an aldehyde group or a protected aldehyde group or an aldehyde precursor group attachment via or a partially rigid spacer as defined above or an at least partially rigid spacer having a chain length of from 2 to 10 atoms is preferred. The structure of a rigid group-containing spacer, e.g. a partially rigid spacer, is preferably such that the rigid group is directly attached to the nucleobase.

The term "nucleotide" according to the present invention particularly relates to ribonucleotides, 2'-deoxyribonucleotides or 2',3'-dideoxyribonucleotides. Nucleotide analogues may be selected from sugar- or backbone modified nucleotides, particularly of nucleotide analogs which can be enzymatically incorporated into nucleic acids. In preferred sugar-modified nucleotides the 2'-OH or H-group of the ribose sugar is replaced by a group selected from OR, R, halo, SH, SR, $NH_2$, NHR, $NR_2$ or CN, wherein R is $C_1$-$C_6$ alkyl, alkenyl or alkynyl and halo is F, Cl, Br or I. The ribose itself can be replaced by other carbocyclic or heterocyclic 5- or 6-membered groups such as a cyclopentane or a cyclohexene group. In preferred backbone modified nucleotides the phospho(tri)ester group may be replaced by a modified group, e.g. by a phosphorothioate group or a H-phosphonate group. Further preferred nucleotide analogues include building blocks for the synthesis of nucleic acid analogs such as morpholino nucleic acids, peptide nucleic acids or locked nucleic acids.

Functionalized nucleic acids may be oligonucleotides, e.g. nucleic acids having a length of up to 30 nucleotide (or nucleotide analogue) building blocks or polynucleotides having a length or more than 30 nucleotide (or nucleotide analogue) building blocks. Preferably, the nucleic acids and nucleic analogues are capable of specific binding to the analyte, e.g. capable of hybridizing with a nucleic acid analyte under assay conditions. The minimum length is preferably 12 and more preferably 14 nucleotide (or nucleotide analogue) building blocks.

Handle groups bound to nucleic acid or nucleic acid analogue building blocks may be incorporated into nucleic acids by standard techniques for chemical synthesis and/or by enzymatic incorporation. Chemical synthesis for example may be carried out by standard phosphoramidite chemistry using modified nucleoside phosphoramidites as building blocks in standard synthesis protocols. Other types of preferred building blocks for chemical synthesis include H-phosphonate or phosphorotriester modified nucleosides.

On the other hand, modified nucleotides may be incorporated into nucleic acids by enzymatic methods. Surprisingly, it was found that handle-modified nucleoside triphosphates are accepted as enzyme substrates by nucleic acid synthesizing enzymes such as DNA polymerases, RNA polymerases, reverse transcriptases or telomerases. For example, it was found that modified nucleoside triphosphates are accepted by DNA polymerases commonly used for primer extension and amplification protocols, e.g. thermostable DNA polymerases such as Taq polymerase, Vent polymerase, Pfx polymerase, Pwo polymerase, or Therminator polymerase. Enzymes accept modified triphosphates without loss in fidelity and allow a template-based incorporation into nucleic acids such as DNA and RNA.

The method of the present invention provides various embodiments of analyte detection. For example, modified nucleic acid building blocks, e.g. nucleotides or nucleotide analogues, together with appropriate enzymes, may be provided which are enzymatically incorporated into a nucleic acid molecule. In the present invention, a plurality of different types of functionalized nucleotides may be employed.

The detection method of the invention may be carried out by any known nucleic acid detection protocols, e.g. involving the use of solid supports. For example, a solid support, e.g. a chip or array or a particulate material such as a bead may be provided to which a capture probe is bound capable of hybridizing to the analyte to be detected. The solid phase bound nucleic acid analyte may be detected by using functionalized hybridization probes which hybridize with the nucleic acid analyte in a different sequence part as the capture probe does and subsequent detection of the bound hybridization probe, e.g. with a metallization reagent. This method is particularly suitable for the diagnostic applications in the agricultural and clinical field, e.g. for the detection of DNA and/or mRNA from plants, e.g. genetically modified plants, DNA from pathogens or plant pests etc., or for brand protection.

In a specific embodiment, the detection may involve contacting an association product of the analyte and a reporter molecule comprising a photosensitizer group with a photosensitive medium, e.g. by transferring a sample or sample aliquot in which an association product may be present onto the photosensitive medium, e.g. by spotting, pipetting etc. Upon irradiation, an energy transfer from the photosensitizer group to the photosensitive medium is effected such that marker groups such as metal, e.g. silver, nuclei are formed in the photosensitive medium in the presence, but not in the absence, of photosensitizer groups. If necessary, the marker groups may be subjected to a development procedure, e.g. a chemical or photochemical development procedure according to photographic techniques. The photosensitive medium may be any solid support or any supported material capable of forming marker groups, e.g. metal nuclei.

Preferably, the photosensitive medium is a light sensitive medium, such as light sensitive paper or a light sensitive emulsion or gel on a supportive material. More preferably the photosensitive medium is a photographic medium such as photographic paper. Irradiation is carried out under conditions, e.g. of wavelengths and/or intensity of irradiation light, under which selective marker group formation takes place in the presence of photosensitizer groups. Preferably, irradiation takes place with infrared light and/or with long wave visible light, depending on the sensitivity of the medium. The irradiation wavelength may be e.g. 500 nm or higher, 520 nm or higher, 540 nm or higher, 560 nm or higher, 580 nm or higher for visible light or 700 nm to 10 µm, for infrared light.

The method of the invention comprises the detection of labelling groups. The labelling groups may be preferably selected from metal deposition-forming groups, e.g. aldehyde-functionalized groups, from fluorescent or fluorescence-forming groups or from redox active groups.

The formation of metal depositions requires the treatment of aldehyde groups with a metallization reagent, e.g. a reagent comprising metal atoms and/or ions selected from Ag, Au, Bi, Cu, Pd or Pt which can be selectively deposited around aldehyde groups, e.g. by reduction. Preferably, the metallization reagent comprises an $Ag^+$ salt such as an Ag-ammonium complex, i.e. the Tollens reagent. Further preferred examples of metallization reagents are $Cu (NO_3)/I_2$, platinum terpyridine complexes such as [Pt(terpy)Cl]Cl, $Pd(OAc)_2$ or $KAuCl_4$.

The detection of the marker groups may be carried out according to known methods. For example, metal depositions may be determined qualitatively and/or quantitatively by optical methods and/or electrical methods. In a preferred embodiment, metal depositions on a solid surface may be determined by measuring electrical parameters, e.g. conductivity. Fluorescent marker groups may be determined qualitatively and/or quantitatively by known fluorescent measurement methods, e.g. excitation via a suitable light source such as a laser and detecting the emitted fluorescent light.

In a further embodiment, the invention comprises the detection of marker groups which are site-specifically formed in a photosensitive medium in the presence of photosensitizer groups. The photosensitizer groups are preferably selected from fluorescent or luminescent groups. The photosensitive medium comprises groups which, when irradiated in the presence of photosensitizer groups, form detectable marker groups such as metal nuclei which can be developed according to standard photographic techniques, e.g. by chemical or photochemical development techniques.

Further, the present invention refers to a conjugate of a nucleic acid or nucleic acid analogue building block with a protected alkyne group, optionally linked by a molecule as shown in Formula (I). Preferably, the spacer has a chain length of 3-10 atoms. Further it is preferred that the spacer comprises internally a rigid group, e.g. an alkyne group. The protected alkyne group is preferably a silyl protected alkyne group as described above.

Further, the present invention refers to a conjugate of a biotin or a biotin derivative such as desthiobiotin or aminobiotin with an azide group optionally linked by a spacer as shown in Formula (II). The spacer has preferably a chain length of 1-10 atoms.

Furthermore, the present invention refers to a conjugate of a quencher group with a nucleic acid or nucleic acid analogue building block, optionally linked by a spacer group as shown in Formula (III). The spacer preferably has a chain length of 3-10 atoms and may comprise an internal rigid, e.g. alkyne group.

Furthermore, the invention refers to the conjugate of a protected aldose group wherein the hydroxic groups of the aldose are preferably protected with acyl and/or silyl groups or of a protected or unprotected 1,2 diol group with a nucleic acid or nucleic acid analogue building block, optionally via a spacer according to Formula (IV). The acyl or silyl protective groups are preferably as described above.

The spacer has preferably a chain length of 3-10 atoms and preferably comprises a rigid group, e.g. an alkyne group.

The invention further relates to compounds of Formula (I), of Formula (II), of Formula (III) as well as of Formula (IV). These compounds can in particular be used for labelling nucleic acids, in particular DNA or RNA. With these compounds, the attachment of one, preferably of at least two functional groups to a molecule is possible. The compounds are in particular useful for DNA-purification, e.g. using a biotin label, for DNA-microarrays, for DNA-chips, for real-time PCR as well as for RNAi experiments and for localisation of DNA in cells.

The invention is described further by the following examples and figures.

FIGURE LEGENDS

FIG. 1: Modified Deoxyribonucleotides for the postsynthetic labelling of DNA.

Figure 2:
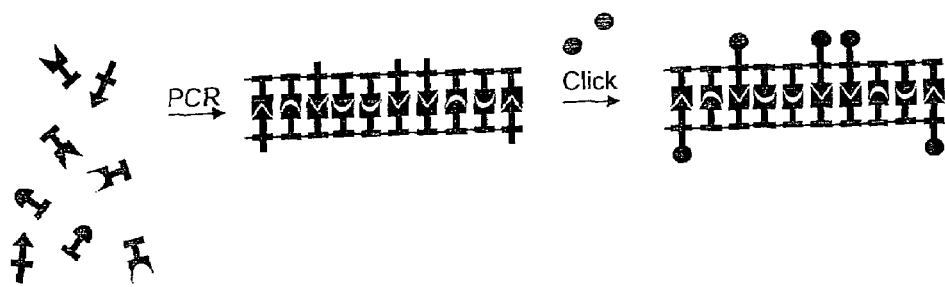

FIG. 2: DNA functionalisation via Click chemistry.

Figure 3:
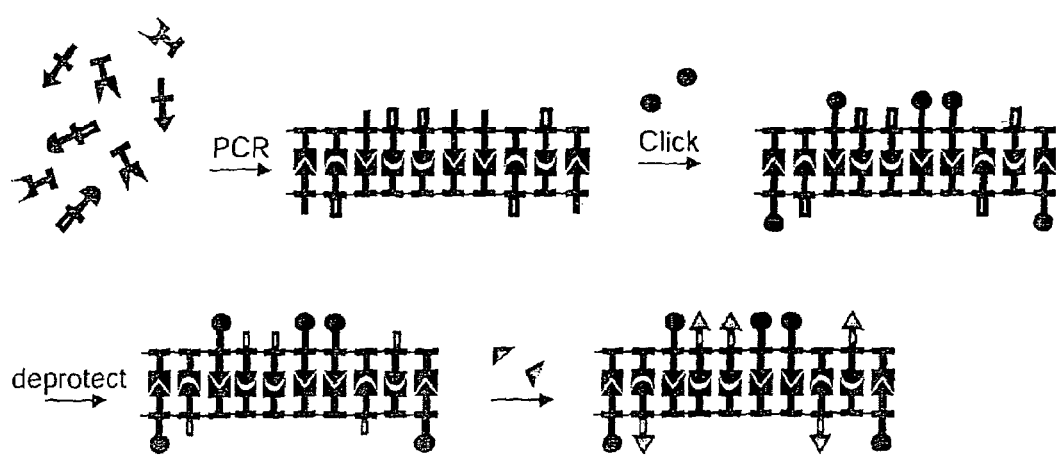

FIG. 3: DNA functionalisation via sequential Click reactions.

Figure 4:
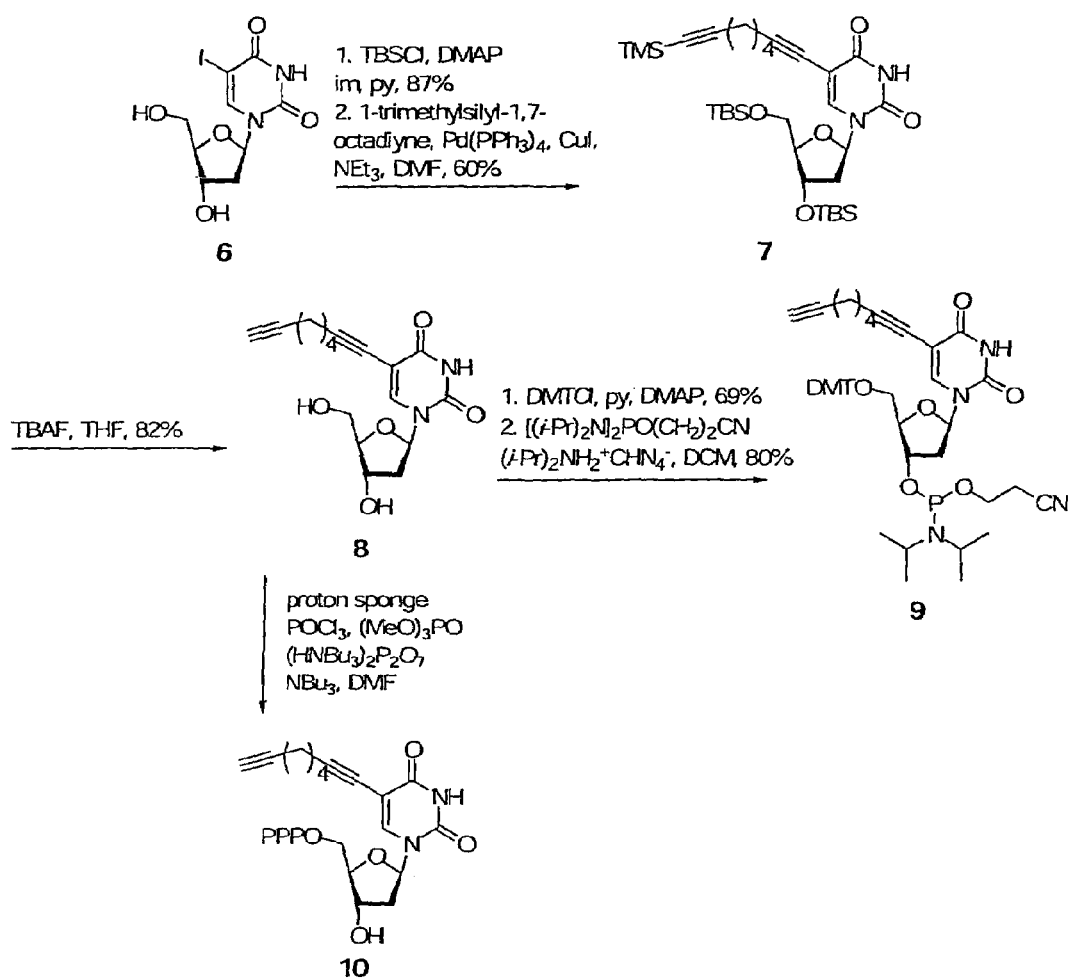

FIG. 4: Synthesis of an alkyne-functionalized 2'-deoxyuridine triphosphate and a phosphoramidite.

Figure 5:
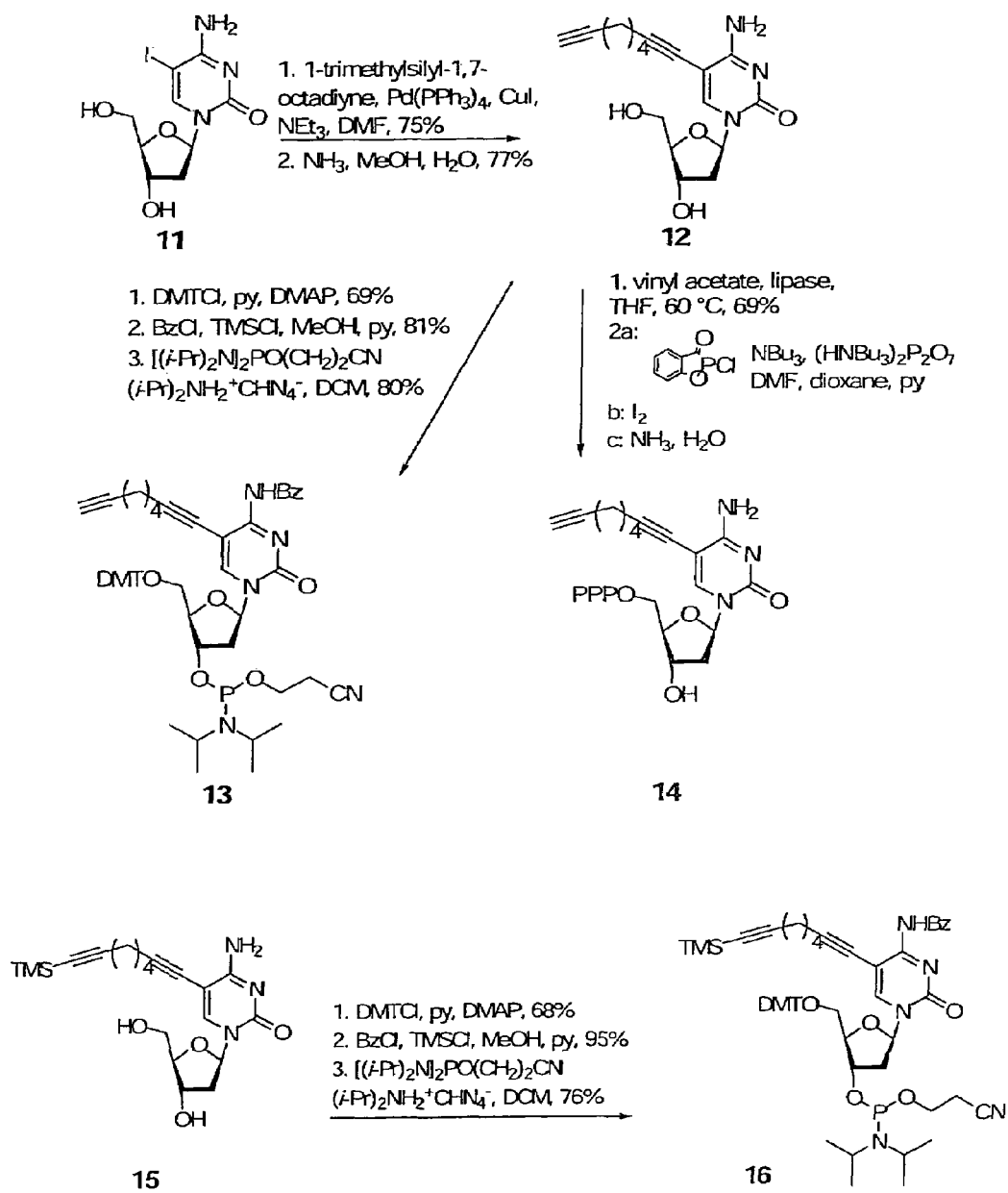

FIG. 5: Synthesis of an alkyne-functionalized 2'-deoxycytidine triphosphate and two phosphoramidites.

Figure 6:
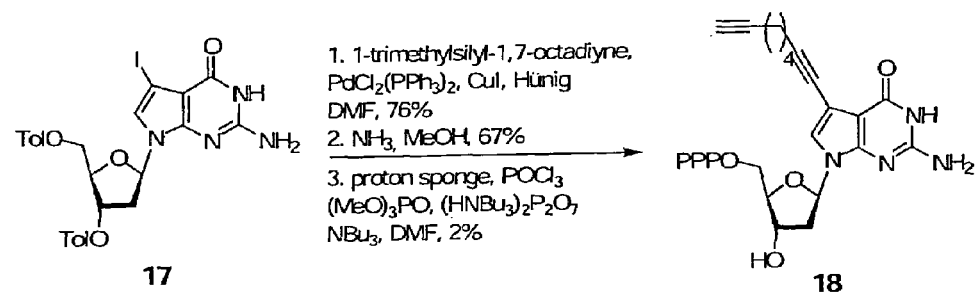

FIG. 6: Synthesis of an alkyne-functionalized 2'-deoxyguanosine triphosphate.

Figure 7:
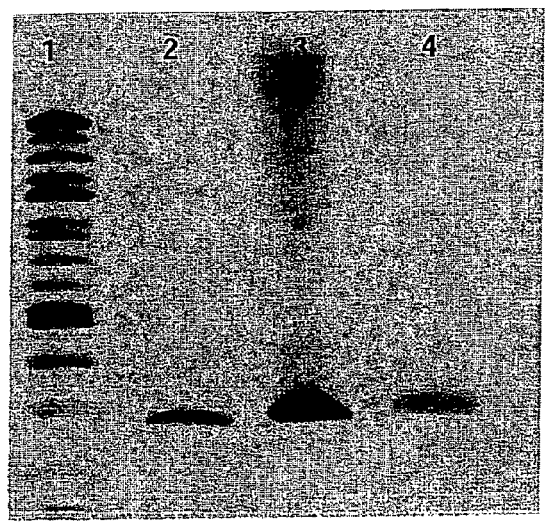

FIG. 7: PAGE-gel electrophoresis (Vent exo–, 0.5 mM $Mg^{2+}$, 50 mM TMAC). Lane 1: 100 bp DNA ladder, lane 2: natural 289 bp fragment, lane 3: same as 2, all thymidines modified, lane 4: all thymidines and cytidines modified.

Figure 8:
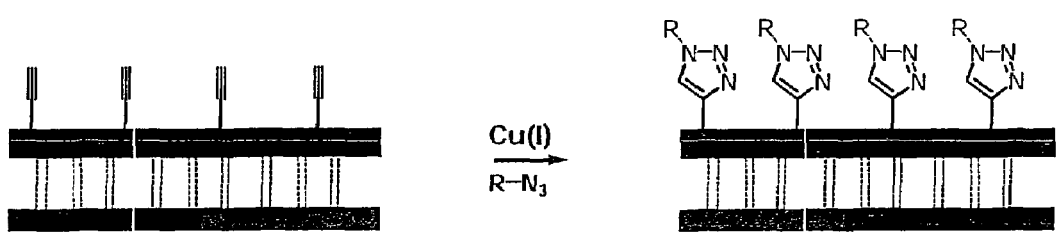

FIG. 8: Click reaction on DNA.

Figure 9:
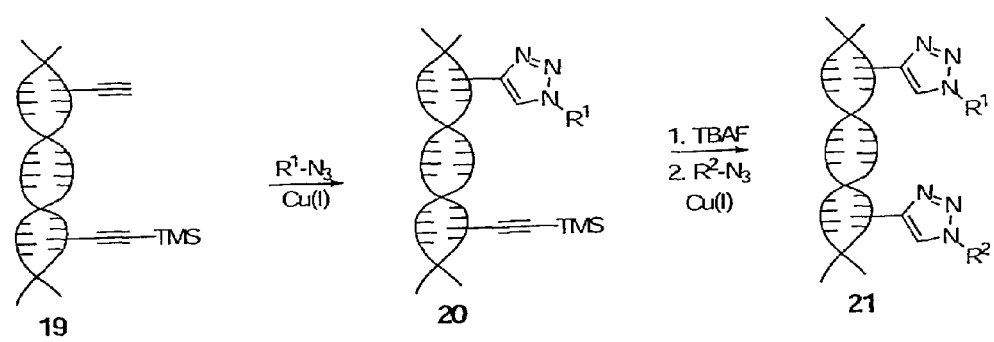

FIG. 9: Reaction sequence yielding oligonucleotides covalently linked to two different molecules (R1-R2).

Figure 10:
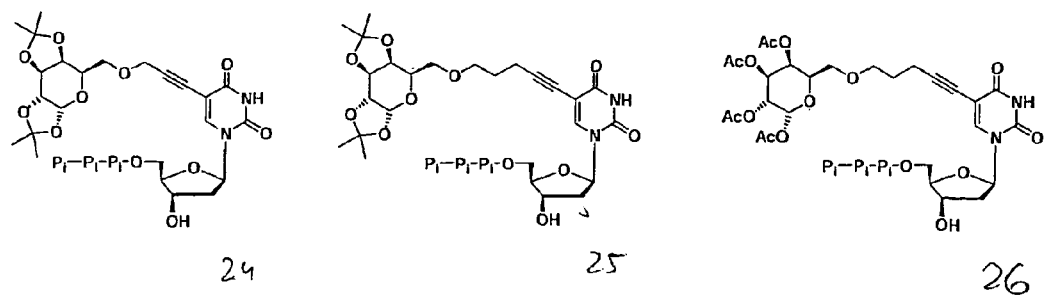

FIG. 10: Sugar-modified nucleotide building blocks.

Figure 11:
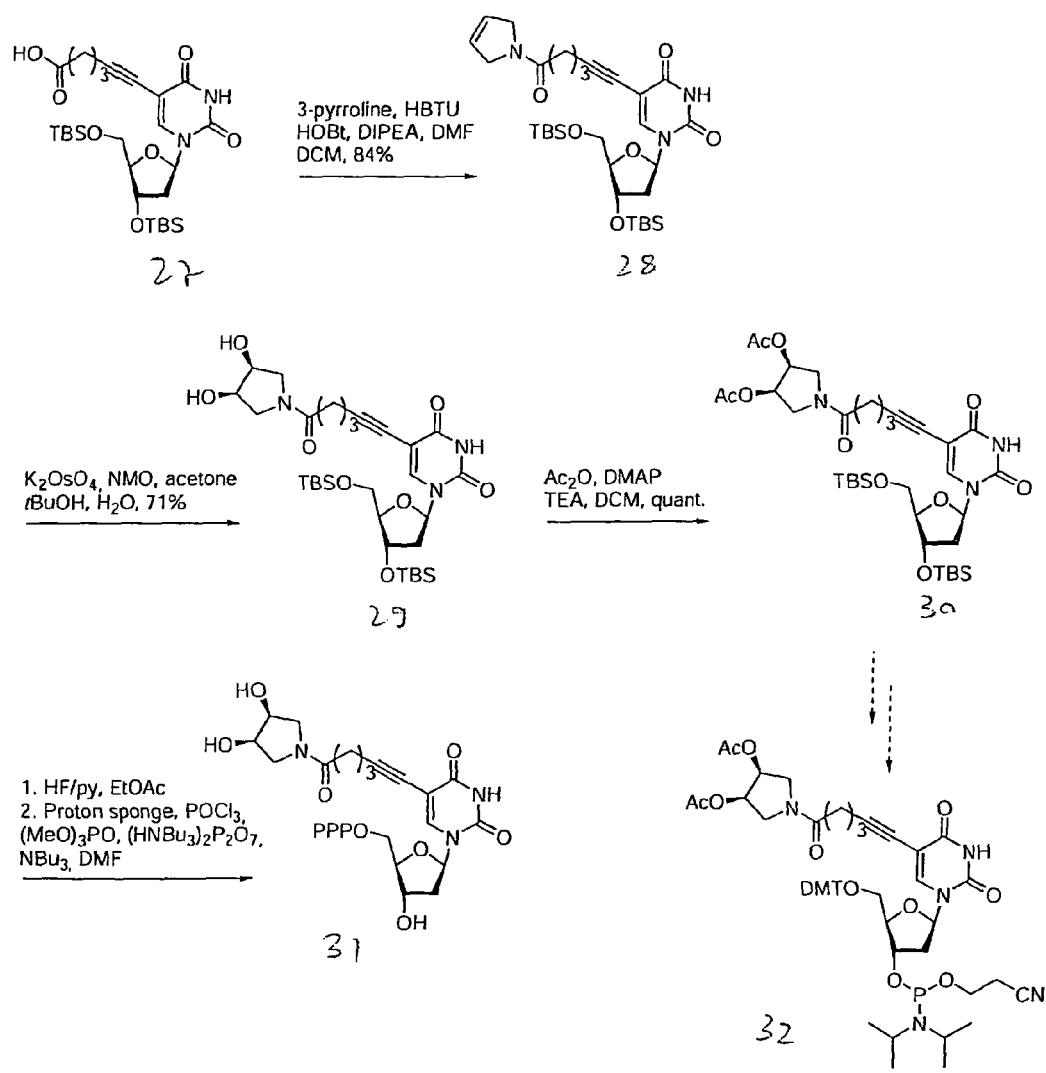

FIG. 11: Synthesis of a cyclic diol-functionalized uridine triphosphate and phosphoramidite.

Figure 12:
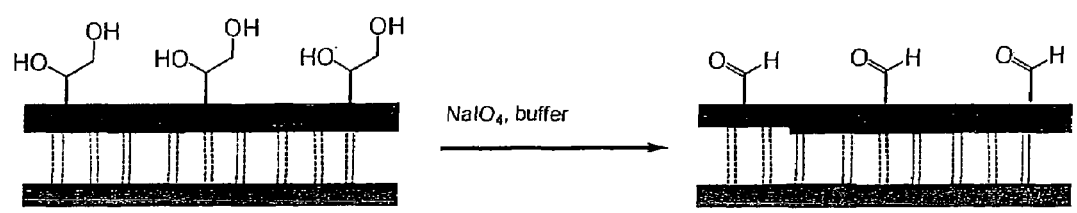

FIG. 12: $NaIO_4$-deprotection of aldehydes.

Figure 13:
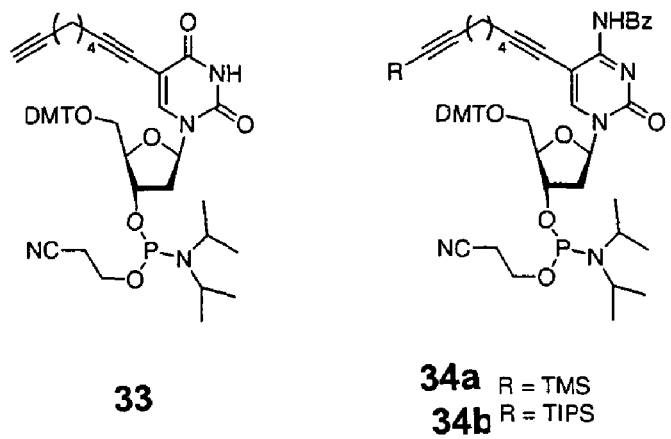

FIG. 13: Alkyne-modified thymidines and cytidine building blocks.

Figure 14:
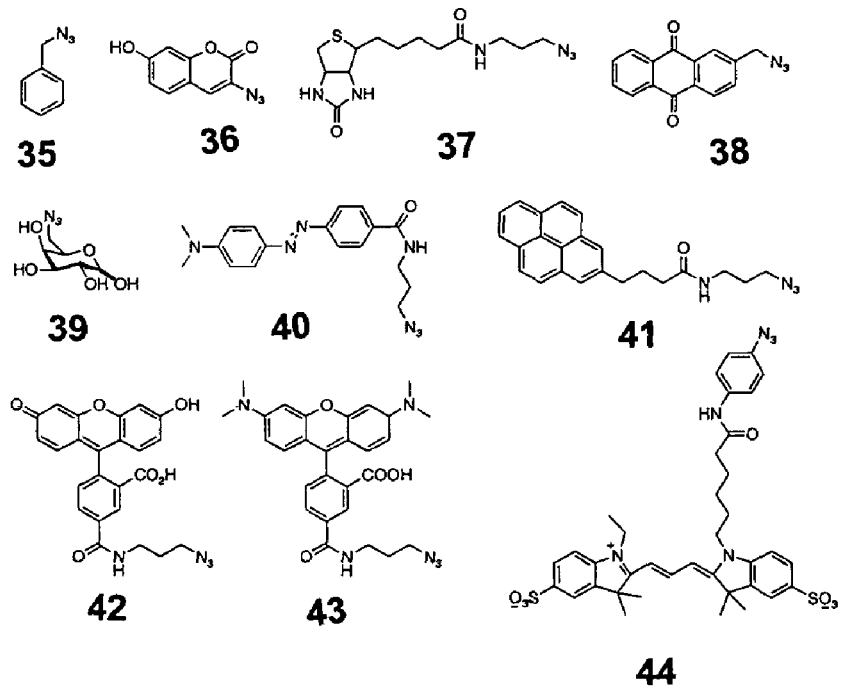

FIG. 14: Azide building blocks. Benzyl azide 35, coumarin azide 36, biotin azide 37, anthraquinone azide 38, galactose azide 39, dabcyl azide 40, pyrene azide 41, fluorescein azide 42, TAMRA azide 43, Cy3 azide 44.

Figure 15:
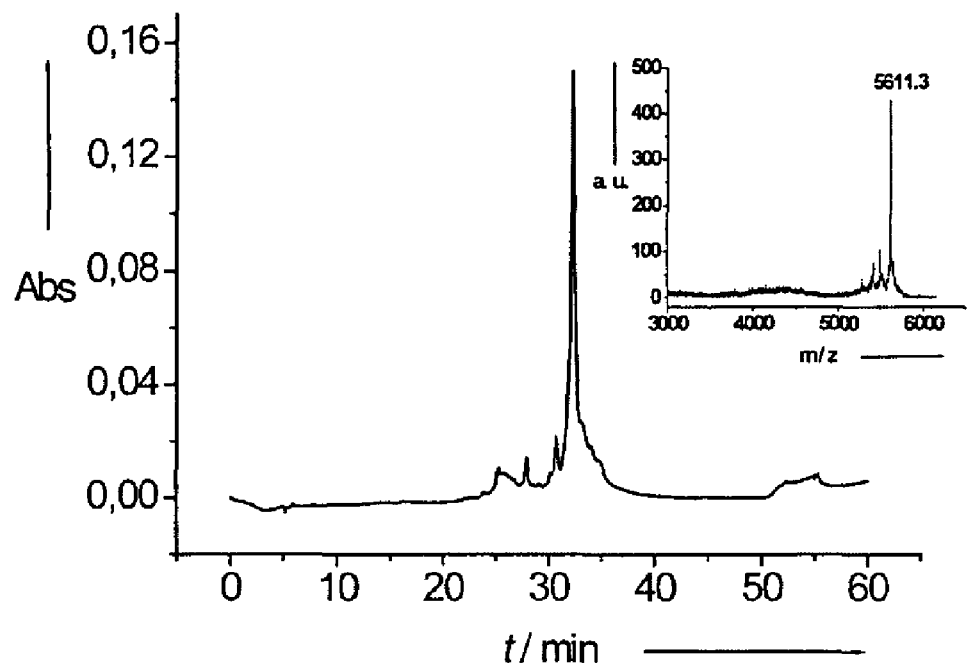

FIG. 15: Crude HPLC trace (260 nm) of an oligonucleotide ODN-3 modified with dabcyl azide 40 and coumarin azide 36 (Table 2, entry 10) and MALDI spectrum (inset).

Figure 16:
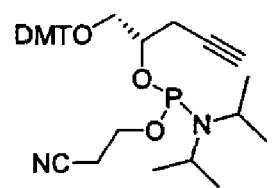
Figure 16:
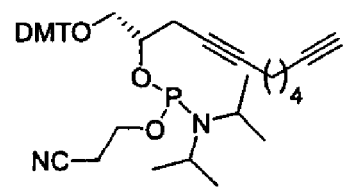

FIG. 16: Non-nucleoside DNA modifiers 13 and 14.

FIG. 17: Schematic representation of nucleic acid functionalization via sequential Click reactions after solid phase synthesis.

FIG. 18: Schematic representation of nucleic acid functionalization via sequential Click reactions after PCR.

EXAMPLES

1. Synthesis of Modified Nucleotide Building Blocks

The synthesis of nucleotide building blocks 1-5 as triphosphates and as phosphoramidites as shown in FIG. 1 can be achieved in short and efficient reaction sequences. DNA synthesis employing these phosphoramidites in standard solid-phase chemistry can be carried out according to standard protocols with the only exception of elongated coupling times for the modified building blocks. The incorporation of the triphosphates via PCR is described in Example 6. These building blocks can be used for the functionalization of reporter molecules, particularly DNA molecules, via the Click chemistry as shown in FIG. 2. Different functional groups may be incorporated via sequential Click reactions as shown in FIG. 3.

2. Synthesis of 2'-deoxyuridine Derivatives Carrying an Alkyne Handle Group

The synthesis of alkyne-functionalized 2'-deoxyuridine-derivatives is schematically depicted in FIG. 4. It starts with the commercially available 5-2'-deoxyiodouridine 6. The free, functionalized nucleoside 8 can be obtained by a standard protection-Sonogashira-deprotection sequence using 1-trimethylsilyl-1,7-octadiyne to introduce the readily functionalised linker in the Sonogashira cross coupling. Phosphoramidite 9 can be obtained using standard procedures. Triphosphate 10 is prepared by the phosphorylation procedure of Yoshikawa [7].

3. Synthesis of 2'-deoxycytidine Derivatives Carrying an Alkyne or a Silyl-Protected Alkyne Handle Group The readily functionalised, free nucleoside 12 can be prepared by a Sonogashira cross coupling on the unprotected and commercially available 5-iodo-2'-deoxycytidine. The TMS group can be removed by treatment with ammonia. Phosphoramidite 13, which is $N^4$-benzoyl protected, is prepared in a stepwise manner. Triphosphate 14 is prepared by the two-step Ludwig-Eckstein procedure [8]. Phosphoramidite 16, bearing a TMS-protected alkyne, is obtained by simply omitting the TMS-deprotection step after the Sonogashira cross coupling. The reaction scheme is shown in FIG. 5. By analogous means a phosphoramidite carrying a TIPS protected alkyne group can be obtained.

4. Synthesis of 2'-deoxyguanosine Derivatives Carrying an Alkyne Handle Group The synthesis of 17 follows the synthesis by Froehler et al. [9]. A standard reaction sequence of Sonogashira cross coupling, global deprotection and phosphorylation by the Yoshikawa [7] approach yields the triphosphate 18. the reaction scheme is shown in FIG. 6.

5. Synthesis of 2'-deoxyadenosine Derivatives Carrying an Alkyne Handle Group The synthesis of modified 2'-deoxyadenosine derivatives 4 is very similar to that of the deoxyguanosine derivatives. It closely resembles the work of Froehler et al. [9]. A Sonogashira cross coupling has been conducted successfully in analogy to the guanosine synthesis. The final steps are similar to those described for derivative 18.

6. Incorporation of Nucleoside Triphosphates Via PCR

The simultaneous incorporation of building blocks 1 and 2 into a 289mer DNA strand was carried out by primer extension. The best incorporation efficiencies were achieved for the triphosphate of 2. The polymerases used are Vent exo– and Pwo from Family B. In the case of a high density of modification the addition of additives (DMSO, formamide, TMAC, betaine) may become necessary. Different levels of alkyne modification can be visualized by PAGE gel electrophoresis. Lanes 2-4 in FIG. 7 show the effect of increasing incorporation of alkynes into DNA. The observed shift is due to an increasing molecular mass of the DNA strands.

7. Postsynthetic Functionalisation

As outlined in the introduction, the main advantage of a postsynthetic labelling strategy is the possibility to introduce labile or reactive moieties into DNA. The molecules to be attached to DNA only have to carry an azide in order to be used in Click reactions. This approach is highly modular and can thus be varied without the need for elaborate syntheses.

The Click reaction has been successfully employed to functionalize DNA at a high-density level. The linkers are sufficiently flexible to allow even for the incorporation of six consecutive modifications by Click reaction, as shown in the modification of a short oligonucleotide bearing six alkyne-modified bases in a row. The reactions are performed in the presence of water and oxygen and do not require any sophisticated equipment. Cu(I) is the active catalytic species and can be stabilized by a ligand. The reaction scheme is shown in FIG. 8.

8. Strategies for Stepwise Functionalisation

8.1 General Considerations

DNA containing two linkers for postsynthetic modification can be prepared using the methodology described above. DNA prepared by PCR is not linked to a resin and does not contain any protecting groups on the nucleobases and can be functionalised in a straightforward manner as outlined in FIG. 9.

Unprotected alkynes can be subjected to a Click reaction with $R^1$-N3. TMS-protected alkynes exhibit sufficient stability to standard Click conditions in test reactions. The TMS-alkyne group can be deprotected with TBAF, thus liberating the free alkyne. Another azide $R^2$—$N_3$ can then be linked to DNA in a second Click reaction.

DNA prepared by solid-phase phosphoramidite chemistry is attached to a resin and carries base-labile protecting groups on the nucleobases. The TMS-alkyne group can be deprotected using ammonia in $H_2O$/MeOH. The preparatively employed deprotection of the silyl group in 15 (FIG. 5) however takes 2-4 days to completion. This remarkable stability could be used to selectively cleave DNA off the resin and/or deprotect the nucleobases without deprotecting substantial amounts of the modified alkynes, e.g. TMS-alkynes. There are, in principle, three ways to address this issue which will be proposed in the following.

8.2 Specific Protocols

For example, oligonucleotides (ODNs) were prepared by the DMT- and β-(cyanoethyl) phosphoramidite method on CPG supports (500 Å) with an Expedite DNA synthesizer (Applied Biosystems) or on an Äkta Oligopilot from Amersham Biosciences. A double coupling protocol (10 equivalents each) was applied for the coupling of modified bases and the coupling time was elongated to 10 min. As activator, benzylthiotetrazole (BTT) gave the best coupling yields. After automated synthesis, ODNs were cleaved from the solid support by soaking in concentrated aqueous ammonia/ethanol solution (3:1) for 24 hours at 25° C. The aqueous ammonia was removed in a SpeedVac, and the crude ODN was purified by RP-HPLC. UVN is spectroscopy and MALDI-TOF mass spectrometry were used to characterize the ODNs.

9. Click Chemistry on the Resin

9.1 General Considerations

Click chemistry can be performed on resins [10]. By the time the first functional group $R^1$ is attached to DNA, a global deprotection of the TMS-groups, the nucleobase protecting groups and the cleavage off the resin can be achieved in one step using ammonia for a prolonged period. At this point, the second functional group $R^2$ can be introduced by a standard Click reaction. In this approach, $R^1$ has to be a base-stable molecule.

9.2 Specific Protocols

For example, approx. 0.02 μmol DNA on CPG resin was dried under high vacuum after DNA synthesis and placed in a 1.5 mL vial together with 20 μL benzyl azide 35. In a separate vial, 40 μL CuBr solution (10 mM in DMSO/tBuOH 3:1), 10 μL sodium ascorbate (100 mM in water) and 80 μL ligand solution (10 mM in DMSO/tBuOH 3:1) were vortexed and added to the DNA. The reaction vial was gently rotated over night, centrifuged and the solution carefully removed and discarded. The resin was washed repeatedly (2×DMSO, 2×$H_2O$, 2× ethanol) by adding the solvent, vortexing, centrifuging and discarding the solution. The DNA was subsequently deprotected as described above.

10. Global DNA Deprotection Prior to the First Click Reaction

DNA nucleobases could be deprotected and the strand cleaved off the resin prior to the first Click reaction (ammonia, 12 h). The stability of the TMS-alkyne to the deprotection conditions should be high enough to retain most of it in intact form. HPLC purification will have to be performed to remove DNA containing deprotected TMS-alkyne sites. From this point onwards, the synthesis outlined in FIG. 9 can be employed.

11. Separate Cleavage Off the Resin

11.1 General Considerations

Click chemistry can also be performed in solution after cleaving the DNA off the resin without removal of protection groups.

The linkage of DNA to the resin is less stable to basic conditions than the nucleobase protecting groups. DNA can thus be cleaved off the resin by treatment with ammonia for 30 minutes. After this treatment the nucleobases are partially deprotected, the TMS-alkyne group should be retained nearly quantitatively. This complex mixture has to be subjected to a Click reaction introducing $R^1$. At this point the DNA can be treated with ammonia for a prolonged period, leading to a global deprotection of the nucleobases and the TMS-alkynes. This step liberates the second Click site, which can be reacted with $R^2$—$N_3$.

11.2 Specific Protocols

DNA (0.38 μM, 200 μL) and azide (10 mM, 114 μL) were placed in a 1.5 mL vial. In a separate vial, 17 μL CuBr solution (100 mM in DMSO/tBuOH 3:1) and 34 μL ligand solution (100 mM in DMSO/tBuOH 3:1) were vortexed and added to the DNA. The solution was shaken at 25° C. for 4 h and evaporated to near-dryness in a SpeedVac. Sodium acetate solution (0.3 M, 100 μL) was added and the suspension left standing for 1 h with occasional vortexing. 1 mL ethanol was added, the vial vortexed and placed in a freezer (−20° C.) over night. After centrifugation (15 min at 13 000 rpm) the supernatant is carefully removed from the DNA pellet. 70% ethanol (−20° C.) was added, the vial vortexed, centrifuged and the supernatant removed. This washing step was repeated twice. After the last washing step the pellet was left drying on air and taken up in water or buffer, as preferred.

11.3 Deprotection of the TIPS-Alkyne Group

Lyophilized DNA was dissolved in dry acetonitrile (400 μL) and dry DMF (100 μL). Two drops of TBAF (1.0 M in THF) were added and the solution shaken at 45° C. for 2 h. Excess fluoride ions are quenched with MeOTMS (10 μL). If an additional Click reaction is to be performed on the DNA strand, the organic solvents should be exchanged to water as follows: the reaction solution is evaporated to near-dryness in a SpeedVac. Water (1 mL) is added, the solution frozen, lyophilized to dryness and taken up in an appropriate amount of water.

12. Synthesis of Sugar-Modified Building Blocks

The triphosphates 22-26 have been successfully incorporated into DNA. The corresponding phosphoramidite of 23 has also been synthesized and incorporated into DNA. The acetyl-protected sugar in compound 26 causes effective staining of the modified DNA in a polyacrylamide gel, as the protecting groups are cleaved under the conditions of the Tollens treatment. The acetonide-protected sugars 24 and 25 need to be deprotected under acidic conditions. Preliminary experiments show that a cleavage of the acetal protecting groups is feasible without causing the depurination of DNA.

In the following, an exemplary synthesis of the cyclic diol modified nucleotide is presented in detail.

The synthesis of the uridine triphosphate 31, modified with a cyclic diol, starts with the known compound 27 [11]. Key step is a Sharpless vicinal dihydroxylation of the pyrroline double bond. From intermediate 30, the phosphoramidite 32 may be synthesized according to known methods.

13. Incorporation of Nucleoside Triphosphates Via PCR

All five presented nucleotides can be incorporated into DNA via PCR, nucleotide 26 even into a 2000 bp strand. The results obtained so far with nucleotide 26 open the way for the effective silver staining of any gene of interest. In principle, it should be possible to synthesize a cytidine modified with a terminal diol and thereby to realize an aldehyde functionalisation of every base pair in DNA.

The incorporation of the triphosphates via enzymatic synthesis, e.g. PCR and the triple click reaction is illustrated in FIG. 18. Preferred polymerases used are Vent exo⁻ and Pwo from Family B. In the case of a high density of modification the addition of additives (DMSO, formamide, TMAC and/or betaine) is preferred. Different levels of alkyne modification can be visualized by PAGE gel electrophoresis.

14. Postsynthetic Functionalization

As shown by chemical synthesis of a DNA strand with a diol-modified uracil, the resulting strands can be treated under mild conditions with $NaIO_4$, giving a smooth cleavage of the diol moieties without any observable side reactions. The aldehyde bearing strands could be characterized by MALDI, as well as by a clean coupling reaction with dinitrophenylhydrazine. Cleavage of long, diol modified DNA strands has been performed, and digestion studies have shown that the cleavage proceeds with comparable efficiency as in short oligonucleotides. First results have been obtained in the coupling of the aldehyde bearing DNA to hydrazine-containing dyes, proving the efficiency of the periodate cleavage.

In the case of the sugar-bearing DNA strands, digestion experiments also show efficient incorporation into DNA. Efficient silver staining has been shown in the case of the acetyl-protected sugar.

New diol-modified nucleotides for direct incorporation into DNA are proposed, as well as new sugar-modified nucleotides. The direct incorporation of these triphosphates into DNA followed by mild postsynthetic deprotection greatly simplifies the silver staining procedures developed in our group. In a combination with "click-click" chemistry, the selective aldehyde modification of our modified DNA by a periodate cleavage could be used to develop a novel triple labelling strategy.

15. Synthesis of a Biotin Azide

Reacting an active ester with 1-amino-3-azidopropan results in the formation of a biotin azide.

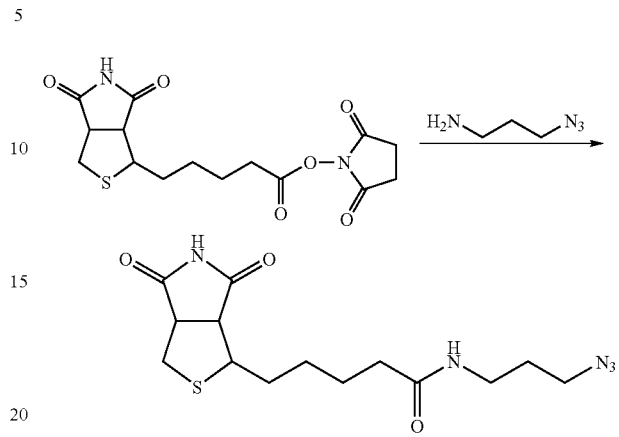

16. Single, Double and Triple DNA Modification with Click Chemistry 16.1 Introduction of Two Different Labels
16.1.1 Double Click Reaction on the Resin A first approach involved the introduction of one free alkyne for the first click reaction and a second TMS-protected alkyne for the second click process after deprotection with mild acid on the resin. To test the feasibility of a click reaction on the resin we prepared a test strand containing one free alkyne 33 and performed the click reaction directly on the resin followed by DNA deprotection. Comparison of the HPLC trace of the functionalized DNA strand with an untreated DNA strand of the same series showed virtually quantitative conversion showing that the click reaction proceeds with high efficiency on the controlled pore glass support used for DNA synthesis (data not shown).

To introduce two labels, we incorporated the thymidine and the cytidine building blocks 33 and 34a into oligonucleotides such as ODN-1 or ODN-2 (Table 1) using standard phosphoramidite chemistry. The coupling yields of both phosphoramidites were excellent. After full assembly of the oligonucleotide on the solid support, the resin was dried and the first click reaction was performed by shaking the resin with a solution of CuBr, TBTA ligand, sodium ascorbate and benzyl azide 35. The resin was washed and rinsed with 1% acetic acid to cleave the TMS protecting group on the second alkyne. Finally the second click reaction was again performed analogously to the first one using dabcyl azide 40. The DNA was finally cleaved from the resin and all protecting groups were removed by exposing the resin to ammonia ($H_2O$/EtOH 3:1). The obtained raw-MALDI spectrum was found to be in full agreement with the expected doubly modified oligonucleotide (Table 2, entry 1) showing that two stable labels can be introduced into DNA directly on the solid support.

16.1.2 Single Click Reaction on the Resin and Combined Cleavage/Deprotection

In some cases it is preferred to perform the second click reaction in solution. Treatment of the singly modified ODN-2 (Table 1) with conc. $NH_3$ in water/ethanol cleaves the DNA from the resin. Under these conditions the base protecting groups and the TMS group, protecting the alkyne, are removed as well. The obtained raw DNA, bearing one clicked-on modification and one free alkyne, is subjected to the second click reaction in solution (CuBr, TBTA ligand, azide), yielding the doubly modified DNA in excellent yields and purity (Table 2, entry 2).

16.1.3 Double Click Reaction in Solution

Oligonucleotides modified with two base and nucleophil sensitive molecules can be readily obtained with the two alkyne bearing building blocks 33 and 34b. Both were incorporated into ODN-3 (Table 1) using standard solid phase phosphoramidite chemistry. After deprotection and cleavage of the oligonucleotide from the resin, the first click reaction was performed (using the solution conditions reported above) yielding the singly modified oligonucleotide with a high yield of >90% on average. In a second step we cleaved the TIPS protecting group with a solution of TBAF in acetonitrile/DMF (4:1 v/v) without causing any damage to the DNA strand bearing one label. The second click reaction in solution yielded the doubly modified oligonucleotides in excellent yields of typically 60-90% over the three-step procedure.

In order to investigate the broad applicability of the double click modification, we performed the double click with a whole series of different labels and found excellent yields for the chemistry on DNA (Table 2, entries 3-15). It is worth mentioning that the individual click reactions and the deprotection steps are so clean that in all cases a simple ethanol precipitation after each reaction step was sufficient for purification. FIG. 15 shows a typical crude HPLC chromatogram and a MALDI analysis (inset) obtained after a double modification of ODN-3. For very sensitive applications one final HPLC purification is recommended. In rare cases such as for Cy3 azide 44 we found that the linker was cleaved to a small extent.

16.2 Introduction of Three Different Labels

Using the click reaction followed by ethanol precipitation it was also possible to modify oligonucleotides with three different labels. To this end we introduced the three building blocks 33, 34a and 34b into oligonucleotides such as ODN-4 (Table 1). The first click reaction was performed directly on the resin. The singly modified oligonucleotide was subsequently cleaved from the support under concomitant cleavage of the TMS group and purified by HPLC. The second click reaction was performed in solution with high yield. Ethanol precipitation of the doubly modified oligonucleotide, cleavage of the TIPS group with TBAF and a subsequent third click reaction in solution furnished the desired triply modified oligonucleotides after a final ethanol precipitation in yields of about 50% (Table 2, entries 16 and 17).

16.3 Introduction of Handle Groups on Non-Nucleoside Building Blocks

Whereas labeling of oligonucleotides directly at certain bases (here dC and dT) is highly desirable, the introduction of labels outside the nucleobases, e.g. on the phosphates or the sugars is frequently needed. In order to allow for easy introduction of labels we prepared the alkyne-bearing non-nucleoside DNA modifiers 37 and 38 (FIG. 16). Click reactions using these building blocks in DNA worked just as efficiently.

16.4 Conclusion

In summary, we report here a highly efficient, modular and robust multiple functionalization protocol of DNA. The efficiency of the method is based on three features: 1. The TMS-protected alkyne is quantitatively removed during ammonia treatment during DNA deprotection. 2. The TIPS-protected alkyne is quantitatively retained during this ammonia treatment. 3. Cleavage of the TIPS protected alkyne can be achieved efficiently and mildly. Synthesis of a triphosphate bearing a protected alkyne allows us to label PCR fragments in a stepwise manner as well. The method will vastly broaden our ability to manipulate DNA as needed for biomolecular diagnostics and nanotechnological applications. In addition, combinatorial syntheses of libraries of multiply modified DNA strands lead to novel aptamers.

TABLE 1

ODNs employed in this study.[a]

| ODN-1 | 5'-GCGCYGTTCATTXGCG-3' | (SEQ ID NO: 1) |
| ODN-2 | 5'-CGCYACACGAAXCCG-3' | (SEQ ID NO: 2) |
| ODN-3 | 5'-GCGCZGTTCATTXGCG-3' | (SEQ ID NO: 3) |
| ODN-4 | 5'-GCGCYGTTXATTZCGC-3' | (SEQ ID NO: 4) |

[a]X = DNA nucleotide based on 1, Y = DNA nucleotide based on 34a, Z = DNA nucleotide based on 34b.

TABLE 2

Post-synthetic labeling of ODNs 1-4.

| Entry | DNA | Label 1 | Label 2 | Label 3 | Yield[a] |
|---|---|---|---|---|---|
| 1 | ODN-1 | 35* | 40* | — | n.a. |
| 2 | ODN-2 | 35* | 36 | — | 75[b] |
| 3 | ODN-3 | 37 | 36 | — | 67 |
| 4 | ODN-3 | 36 | 38 | — | 59 |
| 5 | ODN-3 | 36 | 39 | — | 59 |
| 6 | ODN-3 | 35 | 37 | — | 70 |
| 7 | ODN-3 | 35 | 36 | — | 85 |
| 8 | ODN-3 | 35 | 39 | — | 67 |
| 9 | ODN-3 | 35 | 41 | — | 66 |
| 10 | ODN-3 | 40 | 36 | — | 83 |
| 11 | ODN-3 | 41 | 35 | — | 92 |
| 12 | ODN-3 | 41 | 37 | — | 62 |
| 13 | ODN-3 | 41 | 36 | — | 90 |
| 14 | ODN-3 | 42 | 37 | — | 74 |
| 15 | ODN-3 | 40 | 43 | — | 58 |
| 16 | ODN-4 | 35* | 40 | 39 | 45[c] |
| 17 | ODN-4 | 35* | 39 | 37 | 52[c] |

[a]Determined by integration of the crude HPLC at 260 nm after the last click reaction.

[b]No HPLC purification after cleavage from the resin. Therefore the yield includes impurities from DNA synthesis.

[c]HPLC purification after the click on the resin.

*Click reaction performed on resin.

17. Building Blocks for the Triple Click Reaction in DNA (and RNA)

The synthesis of the ribonucleotides follows the same procedure of the deoxyribo series. All alkynes can be generated as free alkyne, as TMS-protected alkyne or as TIPS-protected alkyne. This gives the access to 12 deoxyribonucleotides-phosphoramidites and 12 deoxyribonucleotides-triphosphates (3 different alkynes per nucleobase) and other 24 for the ribonucleotide series. In addition 6 terminal alkyne phosphoramidites are available as well.

Scheme 1:
Modified Deoxyribonucleotides (or Ribonucleotides) and terminal alkynes for the postsynthetic labelling of DNA.

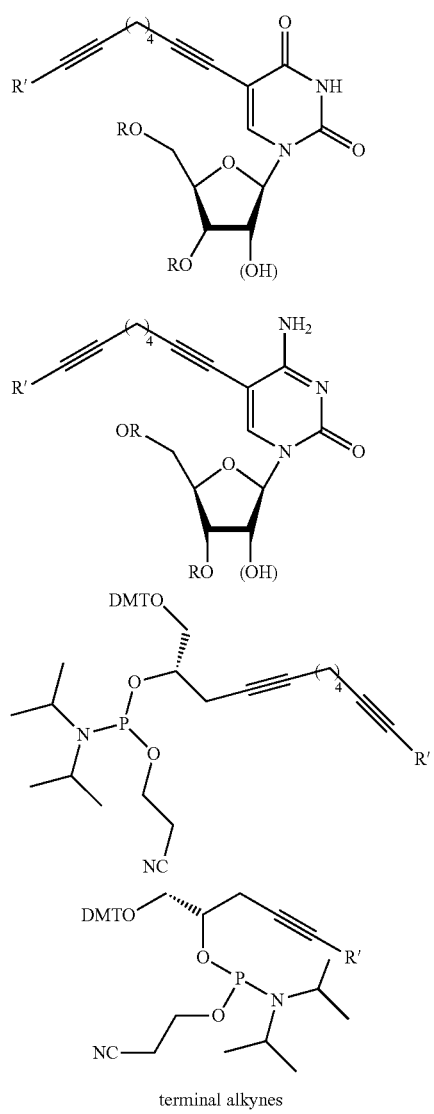

terminal alkynes

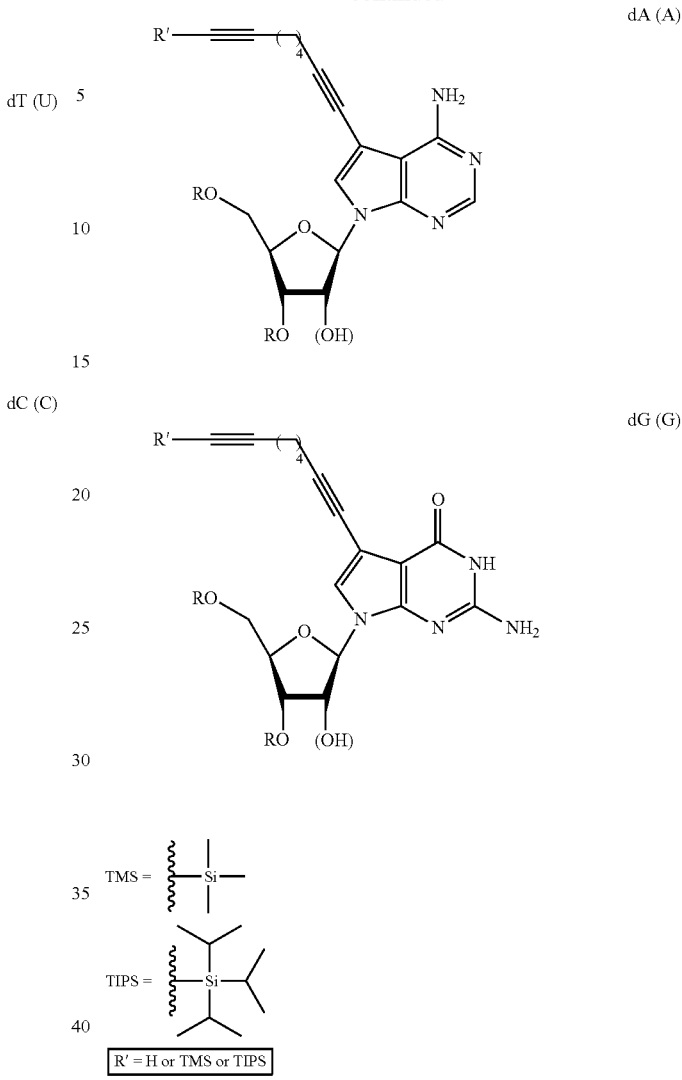

The syntheses of nucleoside building blocks as triphosphates and as phosphoramidites can be achieved in short and efficient reaction sequences. Few examples of these syntheses are reported below.

Synthesis of Uridine Derivatives Bearing a Terminal Alkyne

Scheme 2:
Synthesis of an alkyne-functionalized uridine triphosphate and a phosphoramidite.

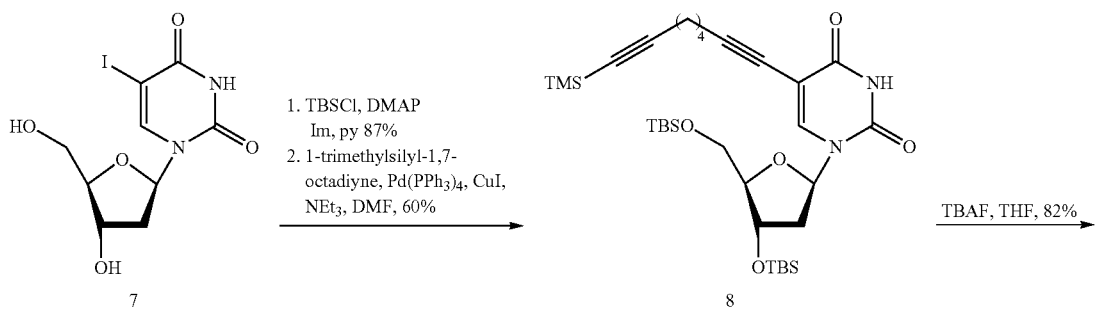

-continued

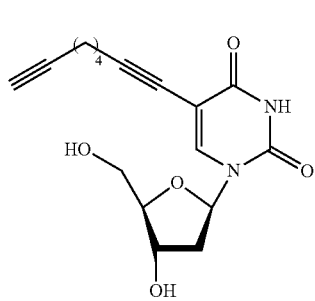

9

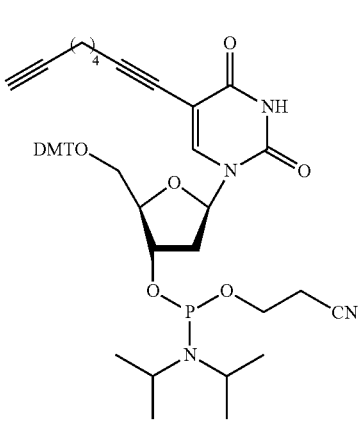

10

1. DMTCl, py, DMAP, 69%
2. [(i-Pr)₂N]₂PO(CH₂)₂CN
   (i-Pr)₂NH₂⁺CHN₄⁻, DCM, 80% proton sponge
POCl₃, (MeO)₃PO
(HNBu₃)₂P₂O₇
NBu₃, DMF

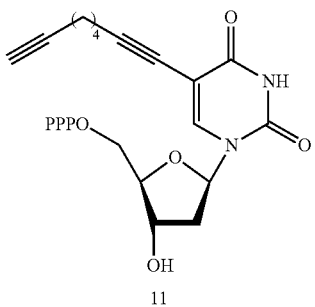

11

The synthesis of alkyne-functionalized uridine-derivatives starts with the commercially available 5-iodouridine 7. The free, functionalized nucleoside 9 can be obtained by a standard protection-Sonogashira-deprotection sequence using 1-trimethylsilyl-1,7-octadiyne to introduce the readily functionalised linker in the Sonogashira cross coupling. Phosphoramidite 10 can be obtained using standard procedures. Triphosphate 11 is prepared by the phosphorylation procedure of Yoshikawa.

Synthesis of Cytidine Derivatives Bearing a Terminal Alkyne and a Silyl-Protected Alkyne Scheme 3:
Synthesis of an alkyne-functionalized cytidine triphosphate and two phosphoramidites.

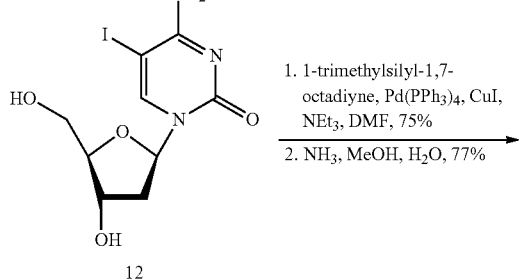

12

1. 1-trimethylsilyl-1,7-octadiyne, Pd(PPh₃)₄, CuI, NEt₃, DMF, 75%
2. NH₃, MeOH, H₂O, 77%

-continued

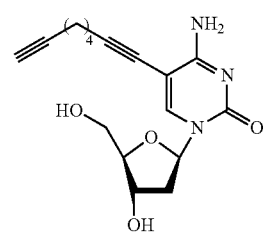

13

1. DMTCl, py, DMAP, 69%
2. BzCl, TMSCl, MeOH, py, 81%
3. [(i-Pr)₂N]₂PO(CH₂)₂CN
   (i-Pr)₂NH₂⁺CHN₄⁻, DCM, 80%

1. vinyl acetate, lipase, THF, 60° C., 69%
2a:

NBu₃, (HNBu₃)₂P₂O₇
DMF, dioxane, py
b: I₂
c: NH₃, H₂O

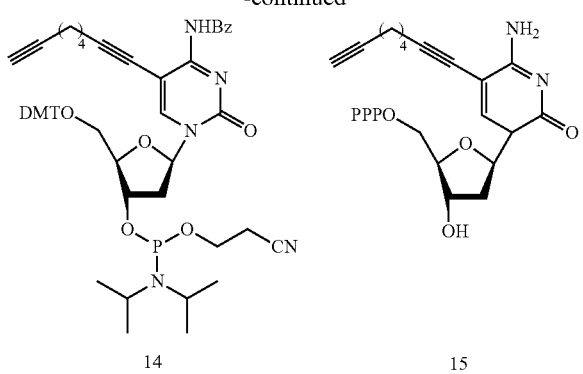
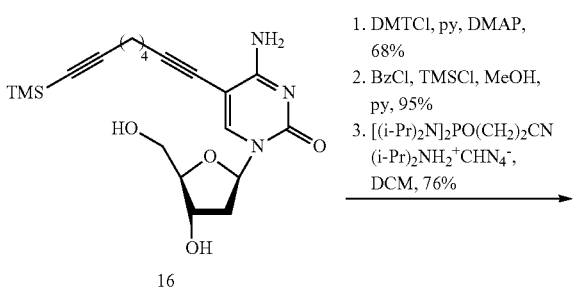
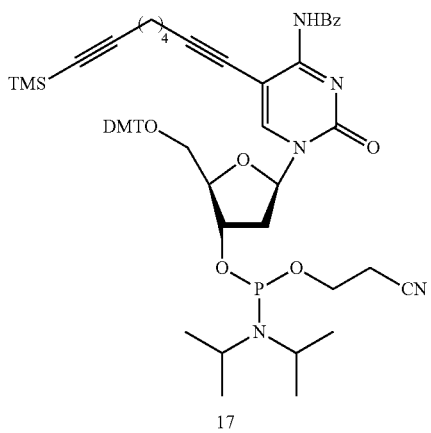

The readily functionalised, free nucleoside 13 can be prepared by a Sonogashira cross coupling on the unprotected and commercially available 5-iodocytidine. The TMS group can be removed by treatment with ammonia. Phosphoramidite 14, which is M-benzoyl protected, is prepared in a stepwise manner. Triphosphate 15 is prepared by the two-step Ludwig-Eckstein procedure. Phosphoramidite 17, bearing a TMS-protected alkyne, is obtained by simply omitting the TMS-deprotection step after the Sonogashira[1] cross coupling.

Synthesis of Guanosine and Adenosine Derivatives Bearing a Terminal Alkyne

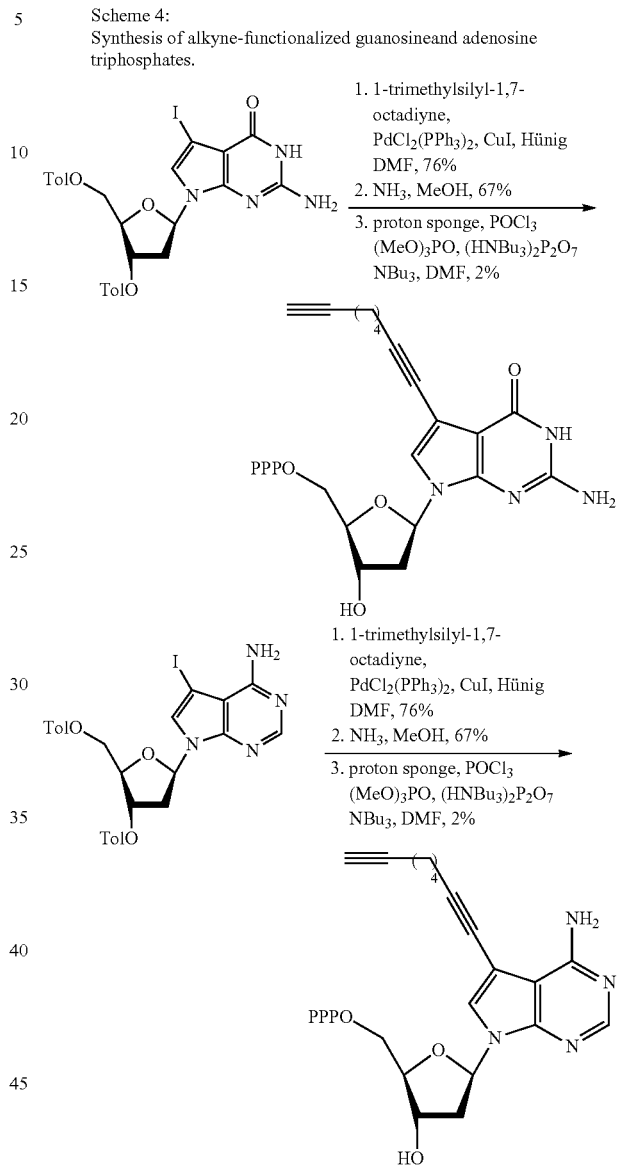

The synthesis of 18 follows the synthesis by Froehler et al. A standard reaction sequence of Sonogashira cross coupling, global deprotection and phosphorylation by the Yoshikawa approach yields the triphosphate 19. The synthesis of modified adenosine derivatives 4 is very similar to that of the guanosine derivatives and is still in progress. It closely resembles the work of Froehler et al. A Sonogashira cross coupling has been conducted successfully in analogy to the guanosine synthesis. The final steps are similar to those described for guanosine-derivative 19.

DNA (or RNA) synthesis employing these modified phosphoramidites in standard solid-phase chemistry is straightforward with the only exception of elongated coupling times for the modified building blocks.

Three different alkynes are used in order to achieve the triple click reaction: one free alkyne, one TMS-protected alkyne and one TIPS-protected alkyne. The first click reaction is carried out still in presence of the resin (the solid support for the automated synthesis). After standard DNA (or RNA)

cleavage from the resin, which removes the TMS groups as well, a second click reaction is achieved using the standard click protocol. A final TBAF (tetra-Butyl ammonium floride) deprotection of the TIPS groups, a third click reaction is carried out (Scheme 4).

18. Example of Modification of a Commercial IR-Dye as Azide

IR-Dyes can be easily transformed into their azide derivatives. The following schemes show two different synthetic pathways out of many other possible syntheses.

In the first case a linker is attached to the dye via a Sonogashira coupling. The following mesylation and azidination produce the azide ready for the click reaction in DNA.

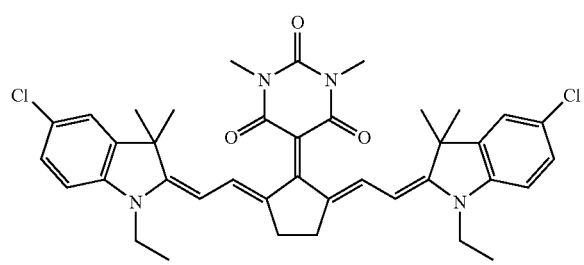

$\lambda_{max} = 777$ nm

Sonogashira-conditions:
BASF-Dye, CuI, Pd(PPh$_3$),
NEt$_3$, 6-Hexinol, DMF, 13 h, RT.
Isomers separation

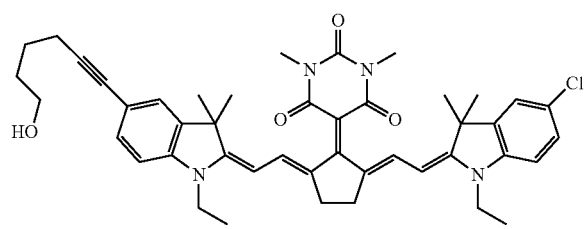

1) MesCl, NEt$_3$, DCM, 30 min, 0° C.
2) NaN$_3$, DMF, 16 h, RT

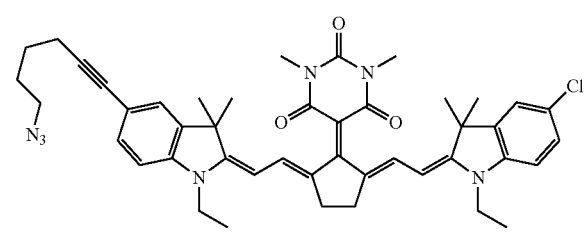

In the second synthesis the azide is generated directly on the dye-core (Scheme 2).

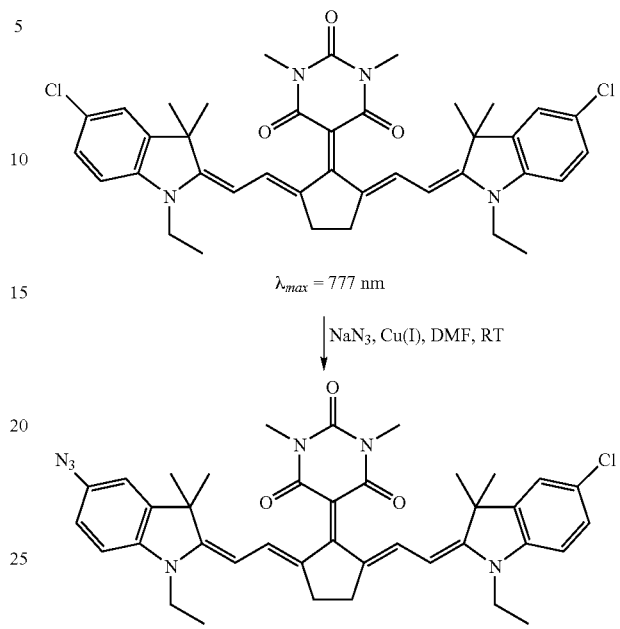

$\lambda_{max} = 777$ nm

NaN$_3$, Cu(I), DMF, RT

IR-Dyes azide can be used in DNA-Photography as photosensitizer of photopaper designed and developed to be sensitized by IR light. Such paper could be handled under normal light condition eliminating the limitation of dark-room conditions.

REFERENCES

[1] Langer, P. R.; Waldrop, A. A.; Ward, D. C. Enzymatic Synthesis of Biotin-Labeled Polynucleotides Novel Nucleic Acid Affinity Probes. Proc. Natl. Acad. Sci. U.S.A. 1981, 78, 6633-6637.
[2] Jäger, S.; Famulok, M. Erzeugung and enzymatische Amplifikation hochgradig funktionalisierter DNA-Doppelstrange. Angew. Chem. 2004, 116, 3399-3403.
[3] Gierlich, J.; Burley, G. A.; Gramlich, P. M. E.; Hammond, D. M.; Carell, T. Click Chemistry as a Reliable Method for the High-Density Postsynthetic Functionalisation of Alkyne-Modified DNA. Org. Lett. 2006, 8, 3639-3642.
[4] Kolb, H. C.; Finn, M. G.; Sharpless, K. B. Click Chemistry: Diverse Chemical Function from a Few Good Reactions. Angew. Chem. Int. Ed. 2001, 40, 2004-2021.
[5] Huisgen, R. 1,3-Dipolar Cycloaddition Chemistry; Wiley: New York, 1984, 1-176.
[6] Aucagne, V.; Leigh, D. A. Chemoselective Formation of Successive Triazole Linkages in One Pot: "Click-Click" Chemistry. Org. Lett. 2006, published online.
[7] Yoshikawa, M.; Kato, T.; Takenishi, T. A Novel Method for Phosphorylation of Nucleosides to 5'-Nucleotides. Tetrahedron Lett. 1967, 8, 5065-5068.
[8] Ludwig, J.; Eckstein, F. Rapid and Efficient Synthesis of Nucleoside 5'-β-(1-Thiotriphosphates), 5'-Triphosphates and 2',3'-Cyclophosphorothioates Using 2-Chloro-4H-1,3, 2-benzodioxaphosphorin-4-one. J. Org. Chem. 1989, 54, 631-635.
[9] Buhr, C. A.; Wagner, R. W.; Grant, D.; Froehler, B. C. Oligodeoxynucleotides Containing C-7 Propyne Analogs of 7-Deaza-2'-deoxyguanosine and 7-Deaza-2'-deoxyadenosine. Nucleic Acids Res. 1996, 24, 2974-2980.
[10] Jang, H.; Fafarman, A.; Holub, J. M.; Kirshenbaum, K. Click to Fit: Versatile Polyvalent Display on a Peptidomimetic Scaffold. Org. Lett. 2005, 7, 1951-1954.

[11] Kahl, J. D.; Greenberg, M. M. Introducing Structural Diversity in Oligonucleotides via Photolabile, Convertible C5-Substituted Nucleotides. J. Am. Chem. Soc. 1999, 121, 597-604.

[12] Tyagi, S.; Kramer, F. R. Molecular Beacons: Probes that Fluoresce upon Hybridization. Nature Biotechnology 1996, 14, 303-308.

[13] Marras, S. A. E.; Kramer, F. R.; Tyagi, S. Efficiencies of fluorescence resonance energy transfer and contact-mediated quenching in oligonucleotide probes. Nucleic Acids Research 2002, 30, e122.

[14] Varma-Basil, M.; El-Hay, H.; Marras, S. A. E.; Hazbon, M. H.; Mann, J. M.; Connell, N. D.; Kramer, F. R.; Alland, D. Molecular Beacons for Multiplex Detection of Four Bacterial Bioterrorism Agents. Clin Chem 2004, 50, 1060-1062.

[15] Tan, W.; Wang, K.; Drake, T. J. Molecular beacons. Current Opinion in Chemical Biology 2004, 8, 547-553.

[16] Marras, S. A. E.; Tyagi, S.; Kramer, F. R. Real-time assays with molecular beacons and other fluorescent nucleic acid hybridization probes. Clinica Chimica Acta 2006, 363, 48-60.

The invention claimed is:

1. A method for producing a reporter molecule comprising at least two different functional groups, said method comprising:
   (a) synthesizing said reporter molecule from a plurality of building blocks, wherein at least one building block comprises a first handle group which is selected from the group consisting of an alkyne group and a protected alkyne group, wherein at least one building block comprises a second handle group which is selected from the group consisting of an alkyne group and a protected alkyne group, and wherein said first handle group is different from said second handle group;
   (b) coupling a first reaction partner to said first handle group under conditions wherein said first handle group is reactive and said second handle group is not reactive, wherein said first reaction partner comprises a first functional group; and subsequently
   (c) coupling a second reaction partner to said second handle group wherein said second reaction partner comprises a second functional group and wherein said first functional group is different from said second functional group, wherein said reporter molecule is selected from the group consisting of nucleic acids and nucleic acid analogues.

2. The method of claim 1, wherein said reporter molecule comprises up to 2000 building blocks.

3. The method of claim 1, wherein said reporter molecule comprises 4-200 building blocks.

4. The method of claim 1, wherein said reporter molecule comprises 10-100 building blocks.

5. The method of claim 1, wherein said functional groups are selected from the group consisting of labelling groups, quencher groups and attachment groups.

6. The method of claim 5, wherein said labelling groups are dyes, and said attachment groups are selected from the group consisting of biotin, biotin derivatives and hapten.

7. The method of claim 1, wherein said first and said second functional groups are a labelling group and a quencher group or wherein said first and said second functional group are a labelling group and an attachment group.

8. The method of claim 1, wherein said handle groups are selected from the group consisting of alkyne groups and protected alkyne groups.

9. The method of claim 8, wherein a reaction partner comprising an azide group is coupled to an alkyne group via Click reaction.

10. The method of claim 1, wherein said first reaction partner is coupled to said first handle group under conditions wherein said first handle group is unprotected and said second handle group is protected.

11. The method of claim 1, wherein at least three handle groups are incorporated into said reporter molecule.

12. The method of claim 1, wherein said first handle group is an alkyne group and said second and third handle groups are protected alkyne groups carrying different protection groups.

13. The method of claim 1, wherein the synthesis of said reporter molecule is a chemical synthesis.

14. The method of claim 13, wherein said synthesis is a chemical solid phase synthesis wherein the reporter molecule is synthesized by stepwise assembly of building blocks while being bound to a solid phase.

15. The method of claim 14, wherein at least the first reaction partner is coupled while said reporter molecule is bound to said solid phase.

16. The method of claim 14, wherein said first reaction partner is coupled after said reporter molecule has been cleaved off said solid phase.

17. The method of claim 1, wherein said reporter molecule is synthesized from nucleoside triphosphate building blocks.

18. The method of claim 1, wherein the protected alkyne group is a tris(alkyl/aryl)silyl protected alkyne.

* * * * *